(12) United States Patent
Nering

(10) Patent No.: US 9,770,317 B2
(45) Date of Patent: Sep. 26, 2017

(54) CURVED SURGICAL FASTENERS FOR SECURING PROSTHETIC DEVICES TO TISSUE

(71) Applicant: Ethicon, Inc., Somerville, NJ (US)

(72) Inventor: Robert Nering, Stockton, NJ (US)

(73) Assignee: Ethicon, Inc., Somerville, NJ (US)

( * ) Notice: Subject to any disclaimer, the term of this patent is extended or adjusted under 35 U.S.C. 154(b) by 114 days.

(21) Appl. No.: 14/587,092

(22) Filed: Dec. 31, 2014

(65) Prior Publication Data
US 2016/0184072 A1   Jun. 30, 2016

(51) Int. Cl.
| | | |
|---|---|---|
| *A61B 17/08* | (2006.01) | |
| *A61F 2/00* | (2006.01) | |
| *A61B 17/064* | (2006.01) | |
| *A61B 17/10* | (2006.01) | |
| *A61B 17/00* | (2006.01) | |
| *A61B 17/068* | (2006.01) | |

(52) U.S. Cl.
CPC .......... *A61F 2/0063* (2013.01); *A61B 17/064* (2013.01); *A61B 17/068* (2013.01); *A61B 17/10* (2013.01); *A61B 2017/00004* (2013.01); *A61B 2017/0649* (2013.01); *A61F 2220/0016* (2013.01)

(58) Field of Classification Search
CPC ........ A61F 2/00; A61F 2/0063; A61B 17/064; A61B 17/10; A61B 2017/0647; A61B 2017/00004; A61B 2017/0649; A61B 17/08; A61B 17/068
See application file for complete search history.

(56) References Cited

U.S. PATENT DOCUMENTS

| | | |
|---|---|---|
| 5,582,616 A | 12/1996 | Bolduc |
| 5,662,683 A | 9/1997 | Kay |
| 5,810,882 A | 9/1998 | Bolduc |
| 5,830,221 A | 11/1998 | Stein et al. |
| 5,935,138 A * | 8/1999 | McJames, II .... A61B 17/06066 606/139 |
| 6,296,656 B1 | 10/2001 | Bolduc |
| 6,562,051 B1 | 5/2003 | Bolduc |
| 7,727,257 B2 * | 6/2010 | Loubens ............ A61B 17/0469 606/223 |
| 8,252,006 B2 | 8/2012 | Ortiz |

(Continued)

FOREIGN PATENT DOCUMENTS

| | | |
|---|---|---|
| EP | 0121362 | 10/1984 |
| EP | 0847727 | 6/1998 |

(Continued)

*Primary Examiner* — Victor Nguyen
(74) *Attorney, Agent, or Firm* — Doherty IP Law Group LLC

(57) ABSTRACT

A curved surgical fastener for anchoring medical devices to tissue includes a curved member having a proximal end and a distal end. The distal end of the curved member has a tissue penetrating end including an insertion tip with a distal point. The curved member has a total curvature of less than 360 degrees between the proximal and distal ends of the curved member. The curved member comprises a compound curve. A proximal section of the curved member has a first radius of curvature and a distal section of the curved member has a second radius of curvature that is different than the first radius of curvature.

12 Claims, 19 Drawing Sheets

(56) References Cited

U.S. PATENT DOCUMENTS

| | | |
|---|---|---|
| 8,388,693 B2 | 3/2013 | Doucet et al. |
| 8,579,919 B2 | 11/2013 | Bolduc |
| 2003/0236551 A1 | 12/2003 | Peterson |
| 2005/0033318 A1 | 2/2005 | Miller |
| 2007/0083235 A1 | 4/2007 | Jervis |
| 2008/0086154 A1* | 4/2008 | Taylor ............... A61B 17/068 606/142 |
| 2008/0097523 A1 | 4/2008 | Bolduc |
| 2008/0234705 A1 | 9/2008 | Cropper et al. |
| 2010/0327042 A1 | 12/2010 | Amid et al. |
| 2013/0090685 A1 | 4/2013 | Gonzales et al. |

FOREIGN PATENT DOCUMENTS

| | | |
|---|---|---|
| EP | 2263559 | 12/2010 |
| WO | 0057796 | 10/2000 |

\* cited by examiner

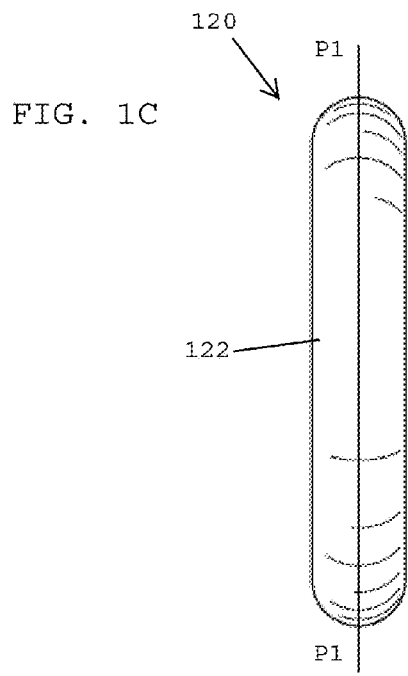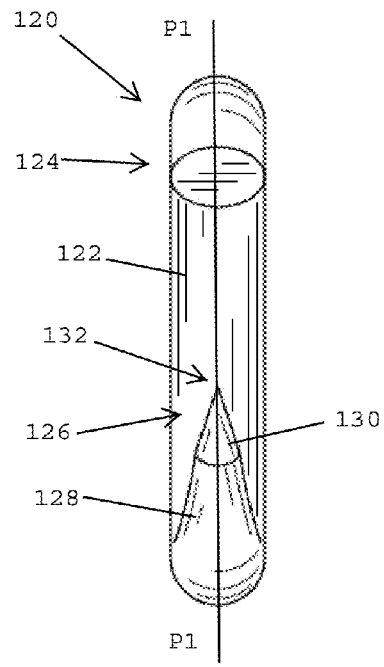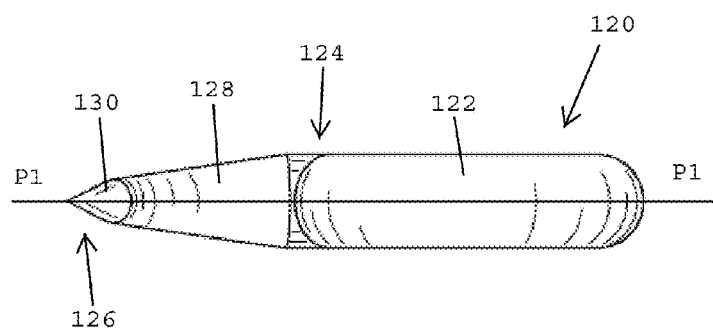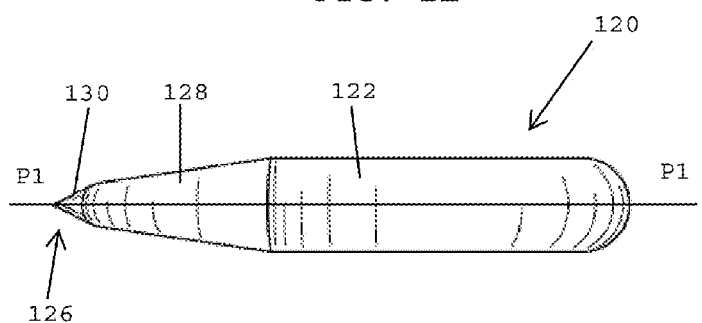

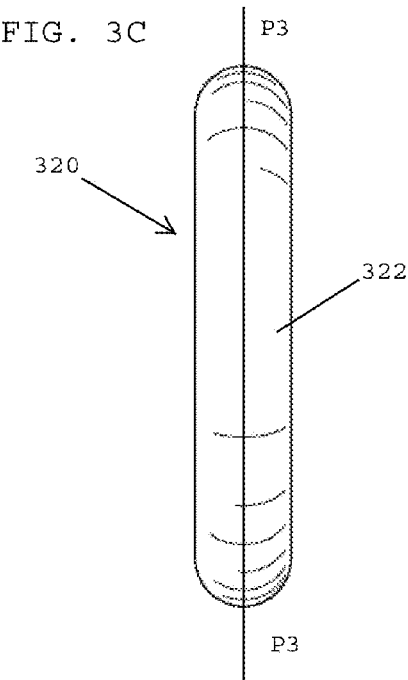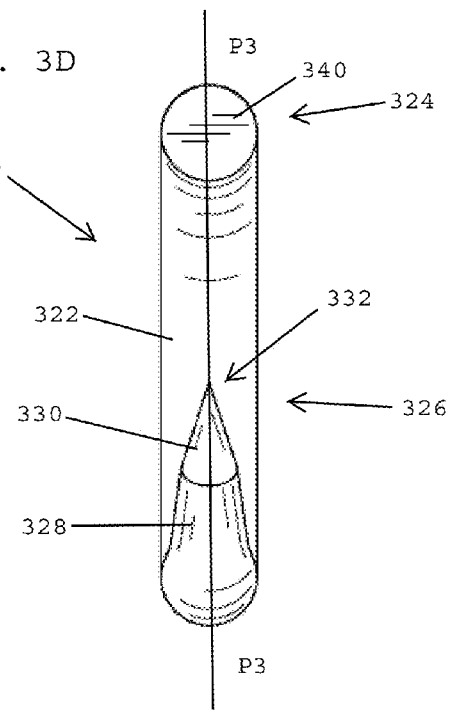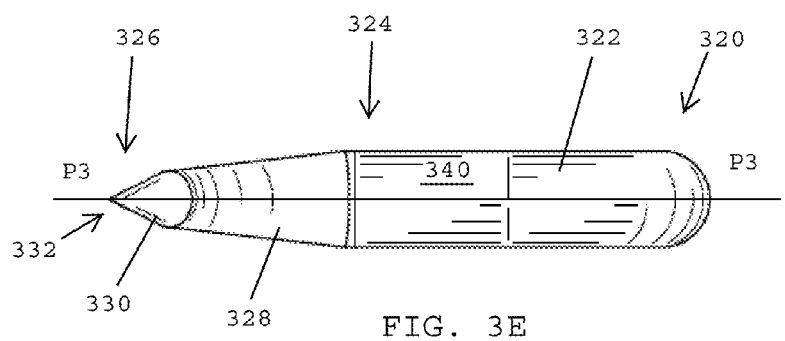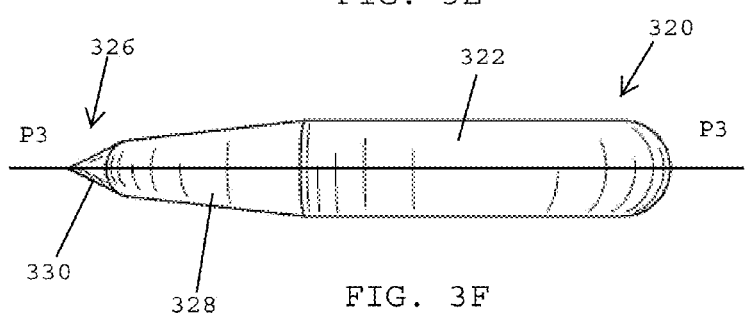

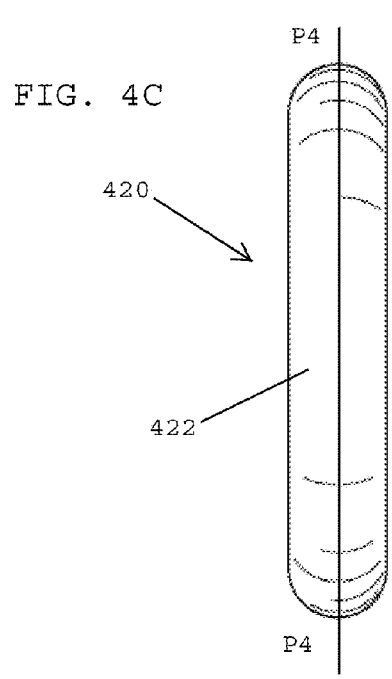
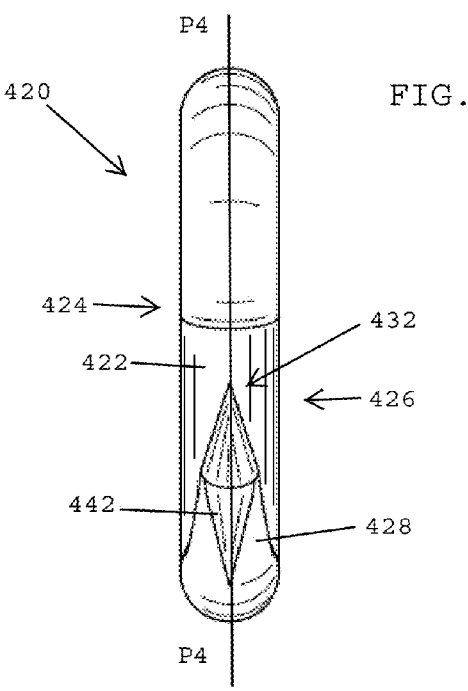
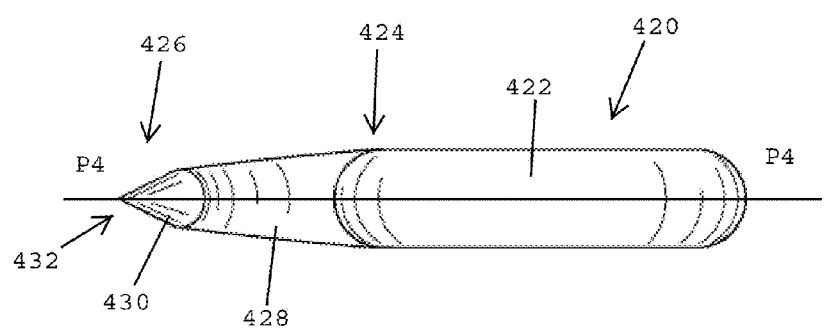
FIG. 4E
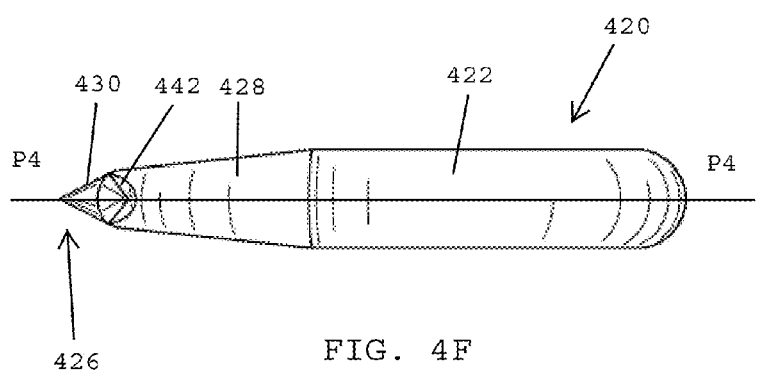
FIG. 4F

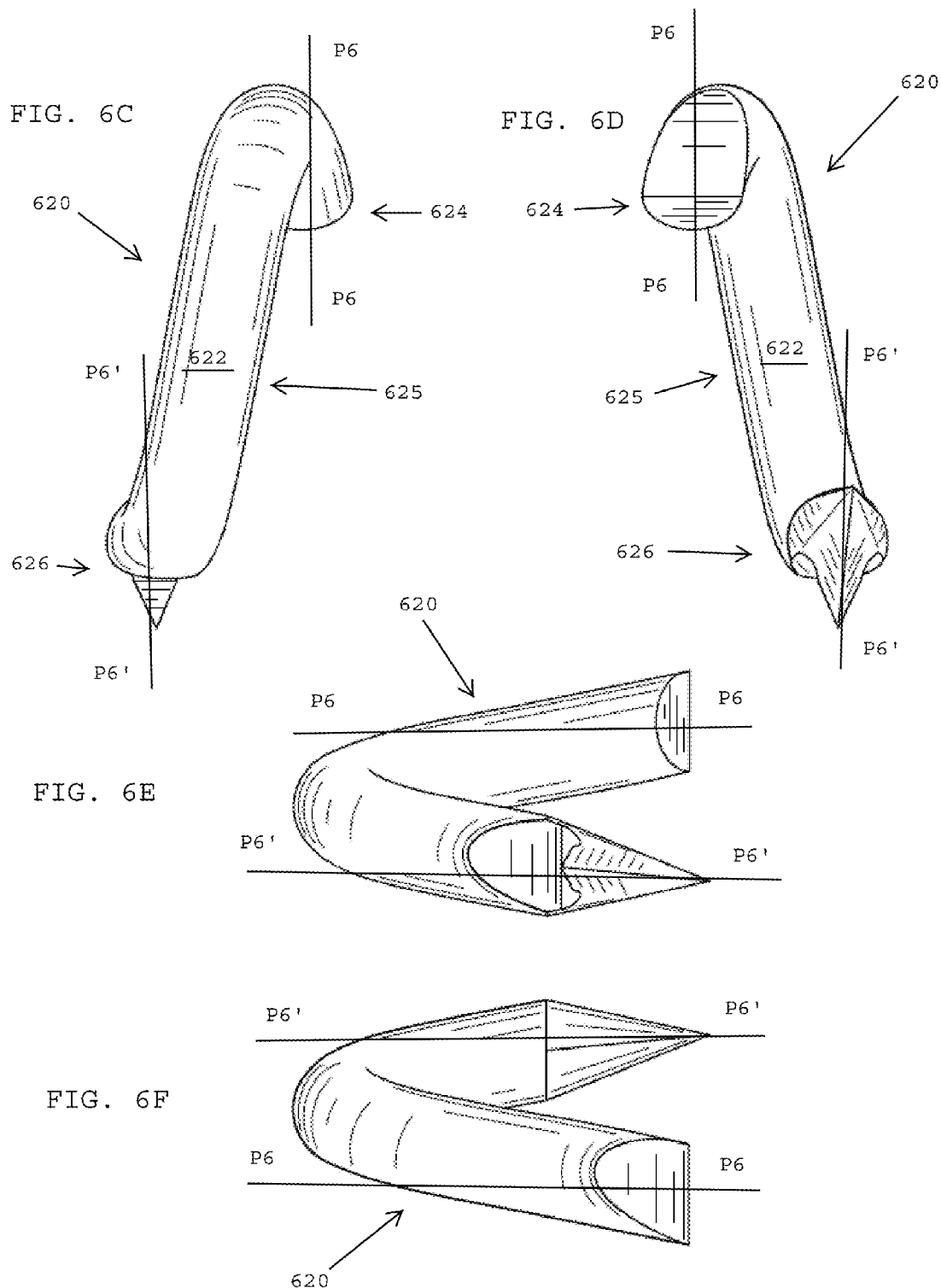

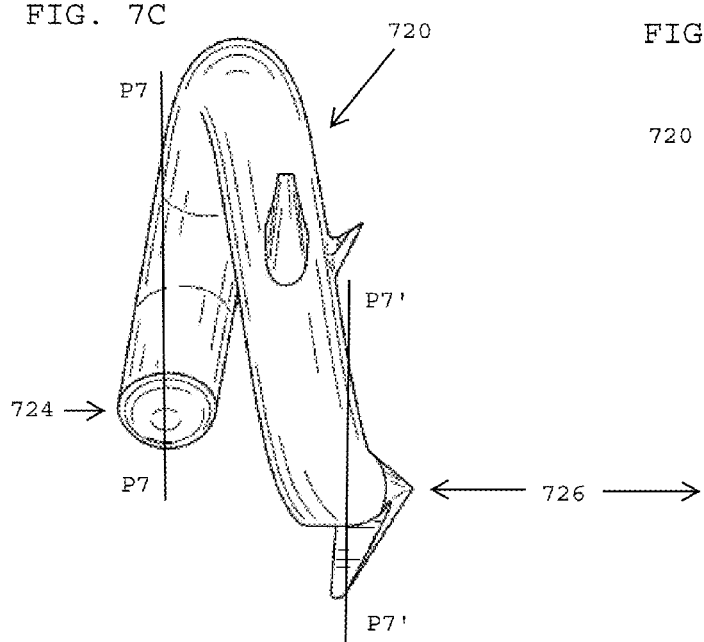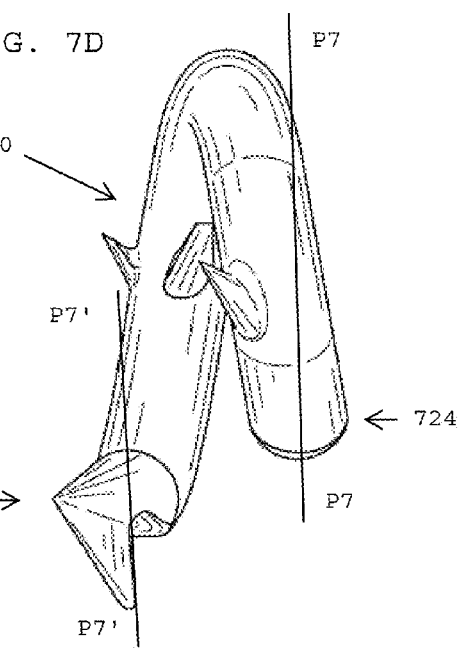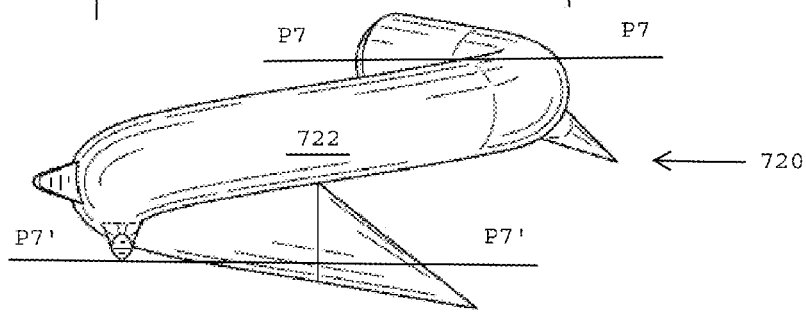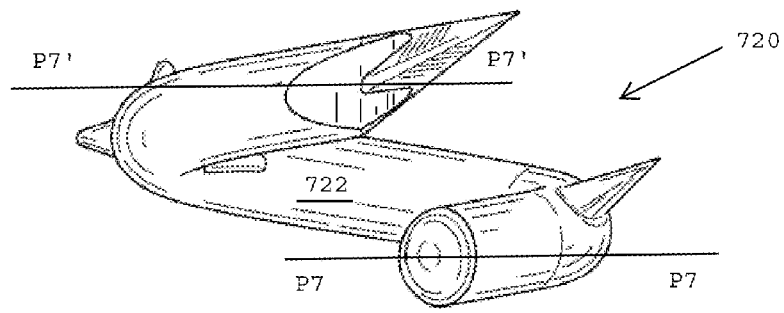

CURVED SURGICAL FASTENERS FOR SECURING PROSTHETIC DEVICES TO TISSUE

CROSS REFERENCE TO RELATED APPLICATIONS

The present patent application is related to commonly assigned U.S. Design patent application Ser. No. 29/509,958, filed Nov. 24, 2014, the disclosure of which is hereby incorporated by reference herein.

BACKGROUND OF THE INVENTION

Field of the Invention

The present invention generally relates to surgical fasteners, and more specifically relates to curved surgical fasteners for securing prosthetic devices such as surgical mesh to tissue.

Description of the Related Art

Hernia is a condition whereby a small loop of bowel or intestine protrudes through a weak place or defect within the abdominal muscle wall or groin of a patient. This condition commonly occurs in humans, particularly males. Hernias may result from a congenital defect whereby the patient is born with this problem, or may be caused by straining or lifting heavy objects. Heavy lifting has been found to create a large amount of stress upon the abdominal wall, which can cause a rupture or tearing at a weak point of the abdominal muscle to create the defect or opening. In any Hernia case, a patient may be left with an unsightly bulge of intestinal tissue protruding through the defect, which may result in pain, reduced lifting abilities, and in some cases, impaction of the bowel, or possibly other complications if the flow of blood is cut off to the protruding tissue.

A common solution for correcting a hernia condition is surgery. During a surgical procedure, the defect is accessed and carefully examined, either through an open incision or endoscopically through an access port such as a trocar. In either case, careful examination is required due to the network of vessels and nerves that exist in the area of a typical defect, which requires a surgeon to conduct a hernia repair with great skill and caution. Within this area can be found vascular structures such as gastric vessels, the external iliac vessels, and the inferior epigastric vessels, as well as reproductive vessels such as the vas deferens extending through the inguinal floor.

Once the surgeon is familiar with the anatomy of a patient, the surgeon carefully places the viscera back into the patient's abdomen through the defect. Repairing the defect can involve closure of the defect with sutures or fasteners but generally involves placing a surgical prosthetic such as a mesh patch over the open defect, and attaching the mesh patch to the abdominal wall or inguinal floor using sutures or surgical fasteners. The mesh patch acts as a barrier and prevents expulsion of bowel through the defect.

Inguinal hernia repair involves the placement and fixation of a surgical mesh over a defect. There are specific sites that must be avoided due to the presence of blood vessels and nerves (known as the triangle of doom and triangle of pain), and specific sites that can be used for mesh fixation (Cooper's ligament, Lacunar ligament, abdominal wall). The Cooper's ligament, also known as the Pectineal ligament, lies on the superior pubic ramus of the pelvis. The thickness of this ligament is typically 1 mm to 3 mm.

Suture is the standard for hernia mesh fixation and is used for affixing mesh to the Cooper's ligament. Suturing of the mesh patch to the inguinal floor can be well suited to open procedures. In laparoscopic procedures, however, suturing is not preferred due to the greater skill and time required.

Adhesives have also been used for hernia mesh fixation, including fibrin and cyanoacrylate adhesives. The use of adhesives has been limited, however, due to high cost, special storage conditions, preparation, and diminished effectiveness on wet tissue.

Self-adhering surgical mesh is also used for laparoscopic hernia repair. Some surgeons have noted some difficulty in handling due to self-adhesion. In addition, surgeons often prefer the additional security of mechanical fixation of the mesh to tissue.

Surgical fasteners are often used during endoscopic or open procedures for attaching mesh patches to the inguinal floor. One of the earliest types of endoscopic procedures involves the use of a surgical stapler that dispenses staples into tissue. The surgical stapler typically has a stack of unformed staples that are contained within a stapling cartridge in a serial fashion. The staples are sequentially advanced or fed within an applicator instrument by a spring mechanism. As the staples are dispensed, an anvil engages the arms of the staple to bend the arms into a closed, clamping position.

Another hernia mesh attachment instrument uses a helical wire fastener that resembles a small section of spring. Multiple helical wire fasteners may be stored serially within a shaft of an applicator instrument, and may be corkscrewed or rotated into tissue. A load spring may be used to bias or feed the plurality of helical fasteners distally within the shaft.

Surgical fasteners have generally been made of metal, such as stainless steel, nitinol, or titanium. The use of metal fasteners was necessary to provide for sufficient holding strength, penetration of various prosthetic meshes, and for ease of manufacture. Although metallic mesh fixation devices are very effective at securing mesh to the Cooper's ligament, it is suspected that metallic devices contribute to long-term patient pain and discomfort.

In response to problems associated with using permanent, metal fasteners, absorbable mesh fixation devices have been developed for securing mesh to tissue. Until recently, there were no absorbable tissue fasteners available on the market, and surgeons could only use absorbable sutures in order to provide a fixation means that did not permanently stay in the body. However, using sutures is exceedingly difficult for laparoscopic procedure, and so they are generally not used unless the repair is done in an open fashion. With surgical trends leading to more minimally invasive techniques with minimum foreign body accumulation, there remains a need for absorbable tissue fasteners for affixing mesh to tissue that can be applied laparoscopically, whereby the tissue fastener has a minimum profile.

Thus, in spite of the above advances, there remains a need for further improvements in surgical fasteners. In particular, there remains a need for surgical fasteners having a minimum profile, surgical fasteners having smaller profiles, surgical fasteners that achieve sufficient anchoring force in tissue, surgical fasteners that may be applied laparoscopically, surgical fasteners that have superior holding strength, surgical fasteners that will not injure vessels and nerves, and surgical fasteners that are absorbable.

SUMMARY OF THE INVENTION

The present patent application discloses a curved surgical fastener for securing a prosthetic device such as a surgical mesh to tissue. In one embodiment, the curved surgical fastener has a curved tissue penetrating point located at the distal-most end thereof. The size and length of the curvature controls the depth of penetration of the curved surgical fastener into tissue, and the pull force required to extract the curved surgical fastener from the tissue. The curvature at the proximal end of the curved member preferably has a captivating geometry that effectively captures a surgical mesh at the proximal end. The captivating geometry may have a radius or tangent section for securing the mesh. The surgical mesh may also be secured at the initial penetration and locked in position by a barb located at the proximal end of the curved surgical fastener. Although the present invention is not limited by any particular theory of operation, it is believed that the embodiments disclosed herein provide low profile shallow depth tissue anchors that effectively secure mesh in areas where tissue thickness is relatively thin or is a concern.

In one embodiment, the curved surgical fastener desirably includes an elongated, curved member having a proximal and a distal end, whereby the curved member has a total curvature of less than 360 degrees extending from the proximal end to the distal end in a first plane. The curved surgical fastener desirably has a tissue penetrating geometry at the distal end and a surgical mesh captivating geometry near the proximal end.

In one embodiment, the curved member includes a compound curve having more than one radius. In one embodiment, the total curvature of the surgical fastener extends into a second plane located above the first plane of the fastener. In one embodiment, the total curvature of the surgical fastener extends into a second plane below the first plane of the fastener.

In one embodiment, the curved surgical fastener has a barb-like feature adjacent the distal end for engaging tissue. The mesh captivating geometry at the proximal end of the curved member may have a radius or a tangent section.

In one embodiment, at least one structural feature, such as a barb, is located on the proximal end of the surgical fastener for capturing a section of the surgical mesh.

In one embodiment, a curved surgical fastener for anchoring medical devices to tissue preferably includes a curved member having a proximal end and a distal end whereby the curved member has a total curvature of less than 360 degrees between the proximal and distal ends. The distal end of the curved member desirably has a tissue penetrating end including an insertion tip having a distal point. In one embodiment, the tissue penetrating end of the curved member may be curved and/or tapered.

In one embodiment, the curved member lies in a single plane. In one embodiment, the proximal end of the curved member lies in a first plane and the distal end of the curved member lies in a second plane that is offset from the first plane. In one embodiment, the curved member has an intermediate section that extends between the first plane at the proximal end of the curved member and the second plane at the distal end of the curved member.

In one embodiment, the curved member comprises a compound curve. In one embodiment, a proximal section of the curved member preferably has a first radius of curvature and a distal section of the curved member preferably has a second radius of curvature that is different than the first radius of curvature. In one embodiment, the first radius of curvature is smaller than the second radius of curvature.

In one embodiment, the proximal end of the curved member includes a tang, such as a straight tang. When the curved surgical fastener is inserted into tissue, the tang preferably engages a surgical mesh for securing the surgical mesh to the tissue.

In one embodiment, the curved member preferably includes one or more barbs projecting therefrom. In one embodiment, the one or more barbs project from the tissue penetrating end of the curved member. In one embodiment, the one or more barbs project from the insertion tip at the distal end of the curved member. The one or more barbs desirably project way from the distal end of the curved member and toward the proximal end of the curved member.

In one embodiment, the curved surgical fastener desirably includes a second barb projecting from the proximal end of the curved member. The second barb preferably projects toward the distal end of the curved member. When the curved surgical fastener is inserted into tissue, the second barb preferably engages a surgical mesh for securing the surgical mesh to the tissue.

In one embodiment, the curved surgical fastener may include one or more supplemental barbs projecting from an intermediate section of the curved member that is located between the proximal and distal ends of the curved member. The one or more supplemental barbs preferably project away from the distal end of the curved member and toward the proximal end of the curved member. When the curved surgical fastener is inserted into tissue, the one or more supplemental barbs preferably engage the tissue for preventing the curved member from being extracted or pulled out of the tissue. In one embodiment, the one or more supplemental barbs include a plurality of barbs projecting from the intermediate section of the curved member.

In one embodiment, a curved surgical fastener for anchoring medical devices to tissue preferably includes a curved member having a proximal end and a distal end, a curved tissue penetrating end at the distal end of the curved member, and a barb projecting from the distal end of the curved member. The curved member desirably has a total curvature of less than 360 degrees between the proximal and distal ends. A proximal section of the curved member desirably has a different radius of curvature than a distal section of the curved member.

In one embodiment, the curved member preferably defines a compound curve with the proximal end of the curved member lying in a first plane and the distal end of the curved member lying in a second plane that is offset from the first plane.

In one embodiment, a curved surgical fastener for anchoring medical devices to tissue desirably includes a curved member having a proximal end and a distal end, the curved member defining a compound curve having a total curvature of less than 360 degrees between the proximal and distal ends of the curved member, whereby the distal end of the curved member includes a tissue penetrating end having an insertion tip with a distal point defining a distal-most end of the curved surgical fastener.

In one embodiment, the surgical fastener is absorbable. The surgical fastener may be made of metal.

In one embodiment of the present invention, the distal points on the insertion tips may have facets. In other embodiment, however, the distal points on the insertion tips may have smooth surfaces such as conical shaped distal points.

In one embodiment, the insertion tips are cut or have defined chisel points, which enable the insertion tips to cut during insertion, thereby improving the ability of the curved surgical fasteners to penetrate difficult materials such as GORE® dual mesh. Insertion tips having compound cut or chiseled angles may also be used to allow for stronger, yet shorter tip designs.

In one embodiment, curved surgical fasteners may have conical-shaped insertion tips that create a puncture rather than a cut, thereby improving holding force. Although the present invention is not limited by any particular theory of operation, it is believed that conical-shaped insertion tips create only a single point of stress concentration, whereby the section of the curved surgical fastener that follows must expand the hole radially. It is believed that this may make it harder for the rest of the curved surgical fastener to make it through the hole, but may potentially increase retention forces by making a tighter hole.

In one embodiment, curved surgical fasteners may incorporate active agents such anti-microbials and anti-adhesion materials. In one embodiment, curved surgical fasteners may incorporate radio-opacity to enable the curved surgical fasteners to be visible on x-ray imaging machines.

These and other preferred embodiments of the present invention will be described in more detail below.

BRIEF DESCRIPTION OF THE DRAWINGS

FIG. 1C is a right side view of the curved surgical fastener shown in FIG. 1A.

FIG. 1D is a left side view of the curved surgical fastener shown in FIG. 1A.

FIG. 1E is a top view of the curved surgical fastener shown in FIG. 1A.

FIG. 1F is a bottom view of the curved surgical fastener shown in FIG. 1A.

FIG. 3C is a right side view of the curved surgical fastener shown in FIG. 3A.

FIG. 3D is a left side view of the curved surgical fastener shown in FIG. 3A.

FIG. 3E is a top plan view of the curved surgical fastener shown in FIG. 3A.

FIG. 3F is a bottom view of the curved surgical fastener shown in FIG. 3A.

FIG. 4C is a right side view of the curved surgical fastener shown in FIG. 4A.

FIG. 4D is a left side view of the curved surgical fastener shown in FIG. 4A.

FIG. 4E is a top plan view of the curved surgical fastener shown in FIG. 4A.

FIG. 4F is a bottom view of the curved surgical fastener shown in FIG. 4A.

FIG. 6C is a right side view of the curved surgical fastener shown in FIG. 6A.

FIG. 6D is a left side view of the curved surgical fastener shown in FIG. 6A.

FIG. 6E is a top plan view of the curved surgical fastener shown in FIG. 6A.

FIG. 6F is a bottom view of the curved surgical fastener shown in FIG. 6A.

FIG. 7C is a right side view of the curved surgical fastener shown in FIG. 7A.

FIG. 7D is a left side view of the curved surgical fastener shown in FIG. 7A.

FIG. 7E is a top plan view of the curved surgical fastener shown in FIG. 7A.

FIG. 7F is a bottom view of the curved surgical fastener shown in FIG. 7A.

DETAILED DESCRIPTION

Figure 1A:
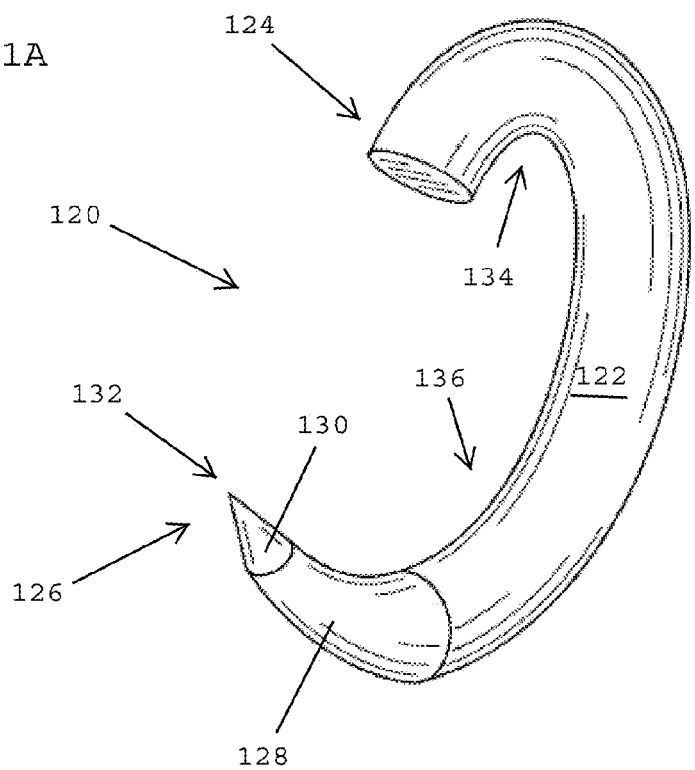
FIG. 1A is a perspective view of a curved surgical fastener, in accordance with one embodiment of the present invention.

Referring to FIGS. 1A-1F, in one embodiment, a curved surgical fastener 120 preferably includes a curved member 122 having a proximal end 124 and a distal end 126. The curved surgical fastener 120 desirably includes a tissue penetrating end 28 located at the distal-most end of the curved member 122. The tissue penetrating end 128 is preferably tapered. In one embodiment, the tissue penetrating end 128 is curved. A distal end of the tissue penetrating end 128 preferably includes an insertion tip 130 having a distal point 132 that facilitates insertion of the tissue penetrating end 128 of the curved member 122 into tissue.

Figure 1B:
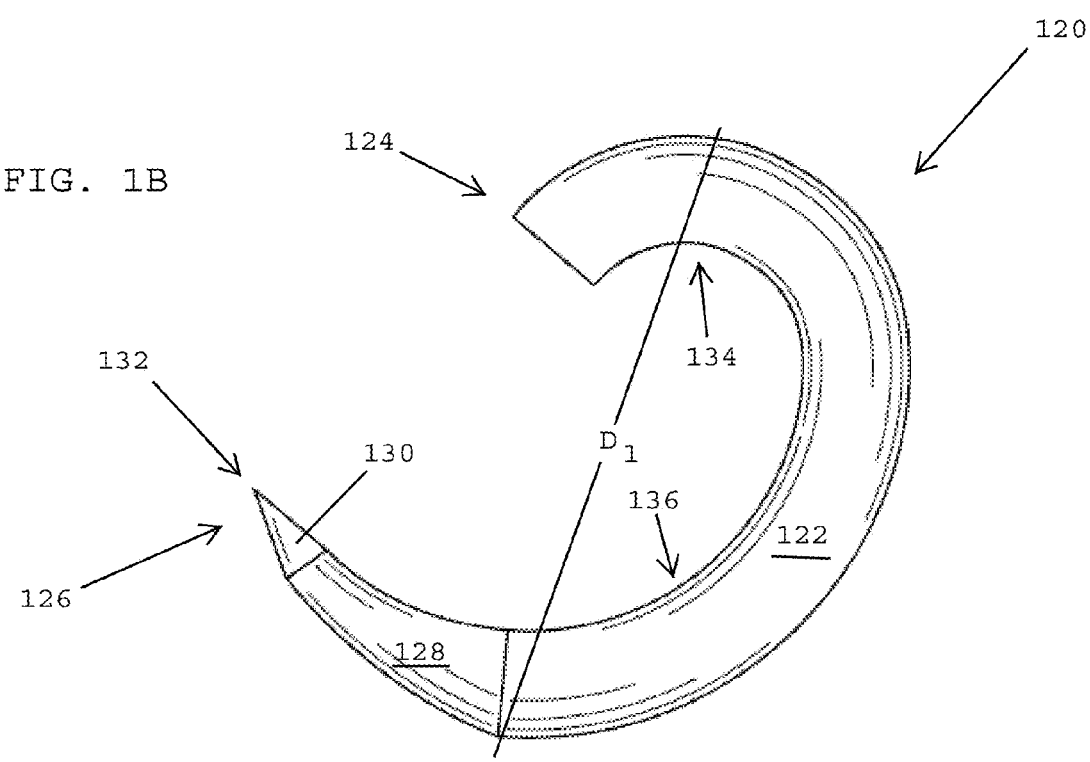
FIG. 1B is a front elevation view of the curved surgical fastener shown in FIG. 1A.

Referring to FIGS. 1A and 1B, in one embodiment, the curved member 122 has a total curvature between the proximal end 124 and the distal end 126 of less than 360 degrees. In one embodiment, the curved member 122 preferably forms a compound curve. As used herein, the terminology compound curve defines a curve made up of two or more circular arcs of successively shorter or longer radii, joined tangentially without reversal of curvature. Compound curves are often used on railroad tracks and highways as an easement curve to provide a less abrupt transition from tangent to full curve or vice versa.

In one embodiment, a proximal section 134 of the curved member 122 has a first radius of curvature and a distal section 136 of the curved member 122 has a second radius of curvature that is different than the first radius of curvature. In one embodiment, the first radius of curvature is smaller than the second radius of curvature. In one embodiment, the first radius of curvature of the proximal section 134 of the curved member 122 is about 1.5 mm, and the second radius of curvature of the distal section 136 of the curved member 122 is about 2.5 mm. In one embodiment, the curved surgical fastener 120 has an outer diameter D1 of about 4.5 mm.

The size and length of the curvature of the curved member 122 preferably controls the penetration depth of the curved surgical fastener into tissue, and the anchoring force exerted by the curved surgical fastener after it has been inserted into tissue. The proximal end 124 of the curved member 122 preferably has a geometry that is adapted to capture a surgical mesh at the proximal end of the device. The geometry at the proximal end 124 of the curved member 122 may have a radius or tangent section for capturing the surgical mesh. The mesh may also be secured via initial penetration of the curved surgical fastener through the mesh, and locked in position by a barb located at the proximal end of the curved member. Although the present invention is not limited by any particular theory of operation, it is believed that the curved designs having a curvature of less than 360 degrees will provide a low profile shallow depth tissue anchor that is suitable for securing surgical mesh in areas where tissue thickness is a concern.

In one embodiment, the curved surgical fastener may be made of absorbable and/or non-absorbable materials. Preferred absorbable materials include PDS, PDS/lactide-glycolide blends, PLA, etc. In one embodiment, each curved surgical fastener is sized to fit inside of a 5 mm outer diameter tube (typically trocar cannula dimension). The curved surgical fastener is fabricated by molding, however, with small modifications, other processes such as casting, stamping, and machining may be used. In one embodiment, the curved surgical fastener may be extruded into a general shape, and then formed.

Referring to FIGS. 1C-1F, in one embodiment, the curved member 122 of the curved surgical fastener 120 lies in a single plane P1.

Referring to FIGS. 2A-2F, in one embodiment, a curved surgical fastener 220 is generally similar to that shown above in FIGS. 1A-1F, but has a curved member 222 having a larger radius of curvature than the device shown in FIGS. 1A-1F. In one embodiment, the curved member 222 has a proximal end 224, a distal end 226, and a tissue penetrating end 228 located at the distal-most end of the curved member 222. The tissue penetrating end 228 is preferably curved and/or tapered. A distal end of the tissue penetrating end 228 desirably has an insertion tip 230 having a point 232 that facilitates insertion of the curved member 222 into tissue.

Figure 2A:
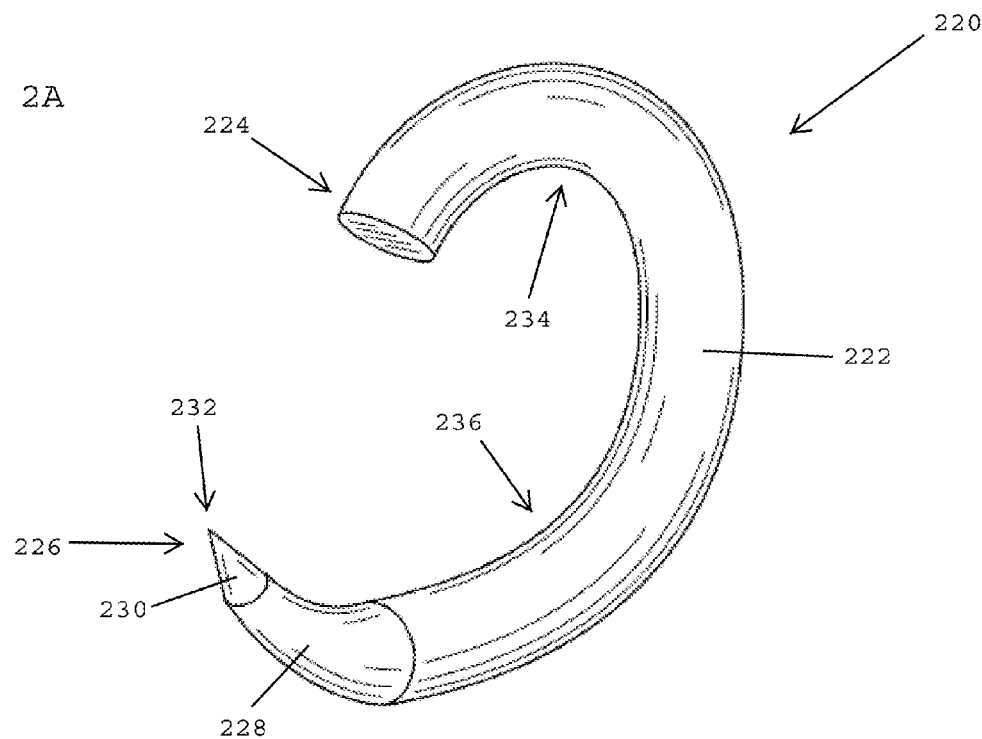
FIG. 2A is a perspective view of a curved surgical fastener, in accordance with a second embodiment of the present invention.
Figure 2B:
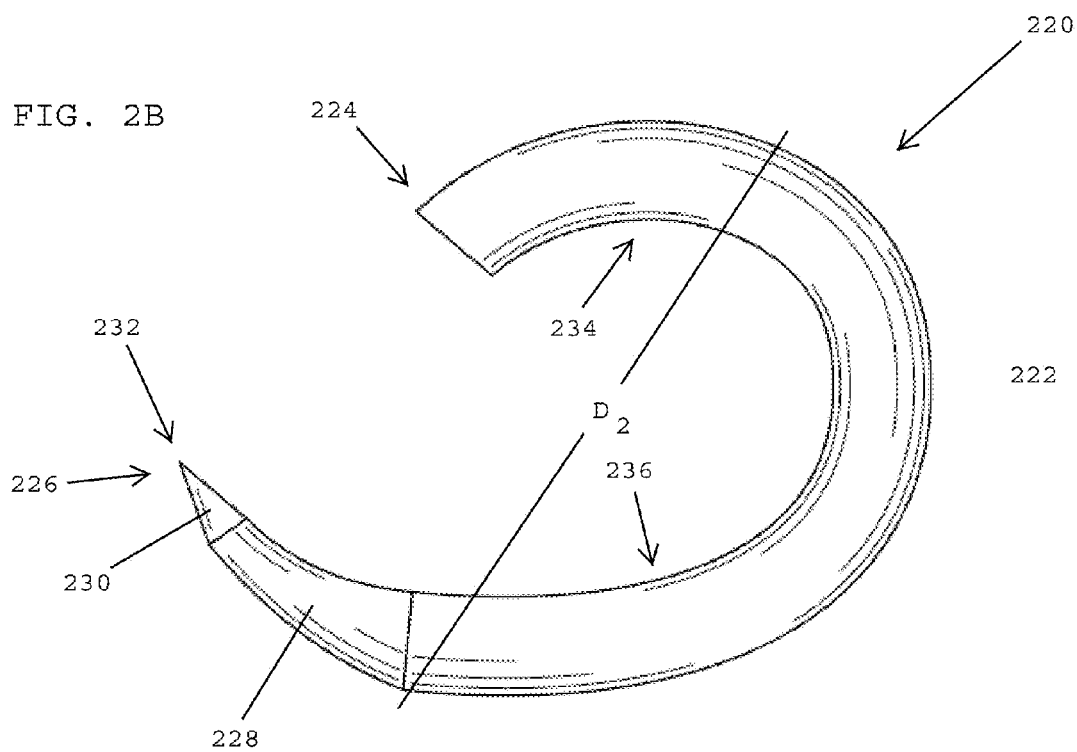
FIG. 2B is a front elevation view of the curved surgical fastener shown in FIG. 2A.
Figure 2C:
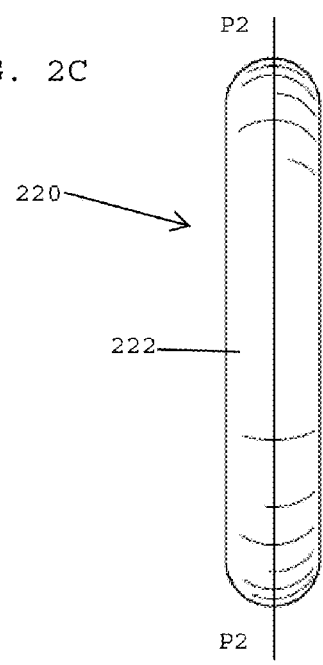
FIG. 2C is a right side view of the curved surgical fastener shown in FIG. 2A.
Figure 2D:
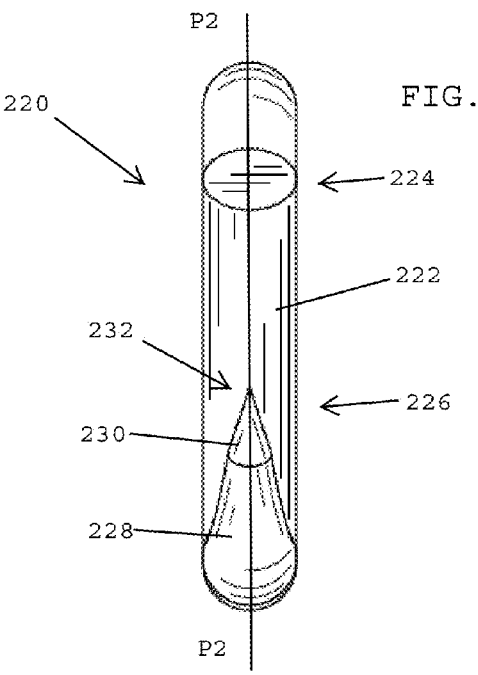
FIG. 2D is a left side view of the curved surgical fastener shown in FIG. 2A.
Figure 2E:
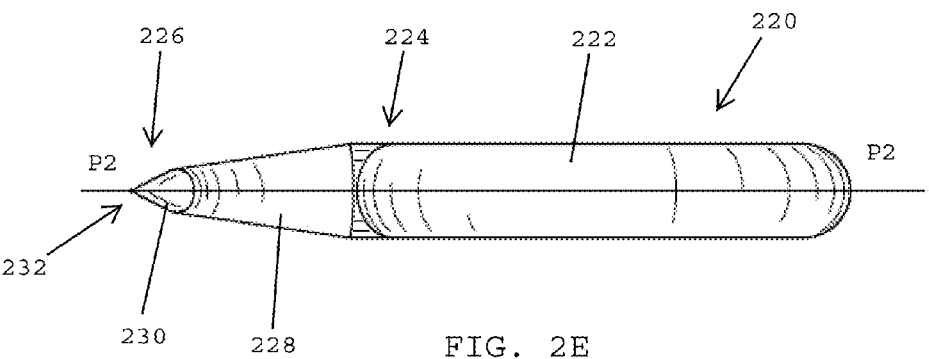
FIG. 2E is a top plan view of the curved surgical fastener shown in FIG. 2A.
Figure 2F:
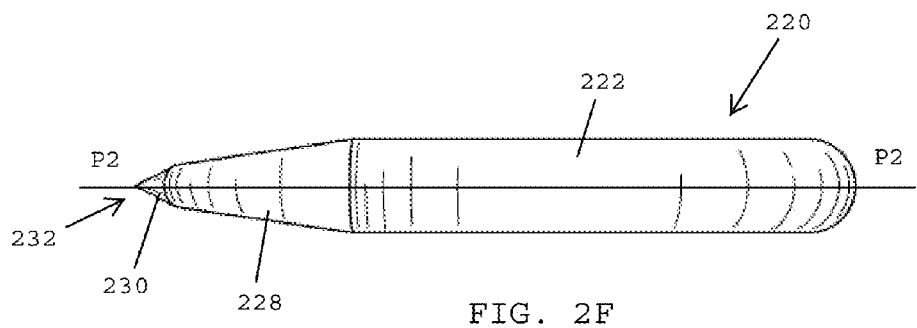
FIG. 2F is a bottom view of the curved surgical fastener shown in FIG. 2A.

Referring to FIGS. 2A and 2B, in one embodiment, the curved member 222 has a total curvature between the proximal end 224 and the distal end 226 of less than 360 degrees. In one embodiment, the curved member 222 defines a compound curve having a proximal section 234 with a first radius of curvature and a distal section 236 with a second radius of curvature that is larger than the first radius of curvature. In one embodiment, the first radius of curvature of the proximal section 234 of the curved member 222 is about 1.5 mm, and the second radius of curvature of the distal section 236 of the curved member 222 is about 2.5 mm. In one embodiment, the curved surgical fastener 220 has an outer diameter D2 of about 4.5 mm.

Referring to FIGS. 2C-2F, in one embodiment, the curved member 222 of the curved surgical fastener 220 lies in a single plane P2.

Referring to FIGS. 3A-3F, in one embodiment, a curved surgical fastener 320 preferably includes a curved member 322 having a proximal end 324 and a distal end 326. The curved surgical fastener 320 desirably includes a tissue penetrating end 328 located at the distal-most end of the curved member 322. The tissue penetrating end 328 is preferably tapered and/or curved. A distal end of the tissue penetrating end 328 preferably has an insertion tip 330 having a distal point 332 that facilitates insertion of the distal end 326 of the curved member 322 into tissue.

Figure 3A:
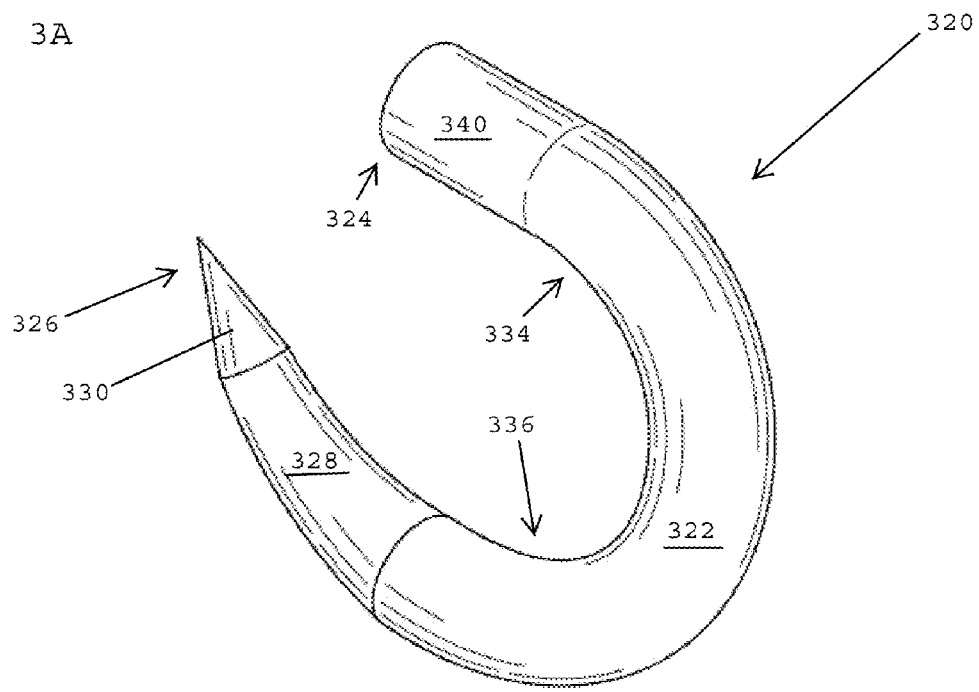
FIG. 3A is a perspective view of a curved surgical fastener, in accordance with a third embodiment of the present invention.
Figure 3B:
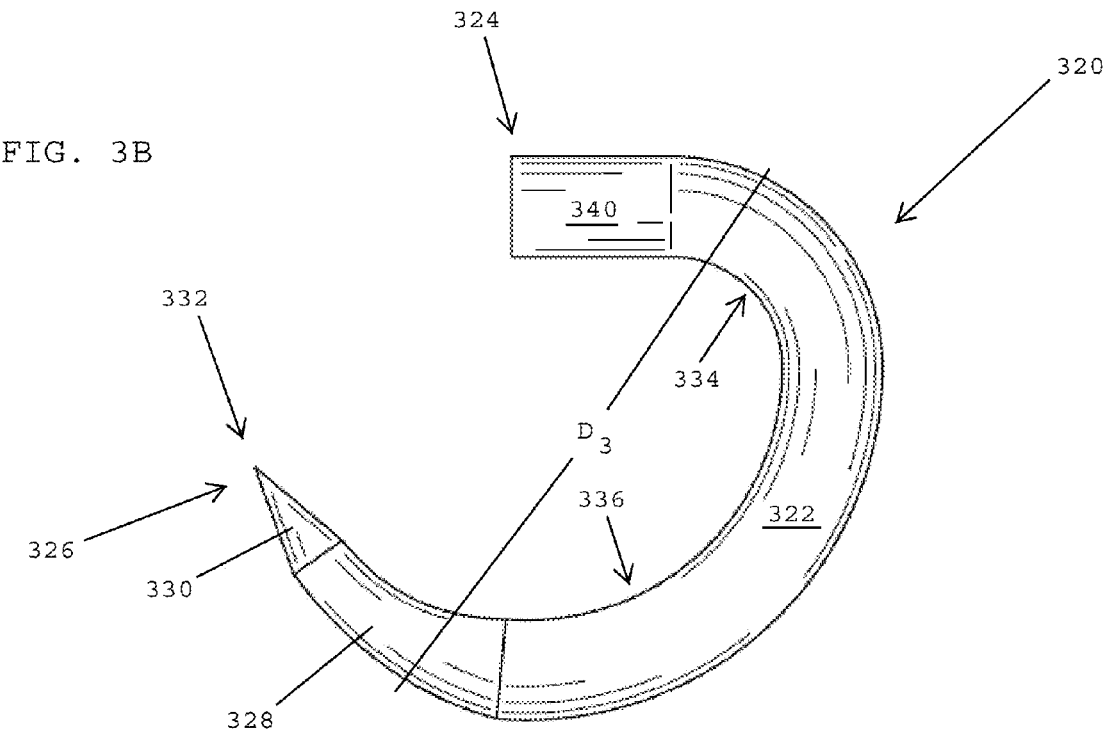
FIG. 3B is a front elevation view of the curved surgical fastener shown in FIG. 3A.

Referring to FIGS. 3A and 3B, in one embodiment, the proximal end 324 of the curved member 322 has a tang 340 projecting therefrom. The tang 340 may define a straight section of the device 320 and is adapted to engage a surgical mesh for securing the surgical mesh to tissue.

In one embodiment, the curved member 322 has a total curvature between the proximal end 324 and the distal end 326 of less than 360 degrees. In one embodiment, the curved member 322 is a compound curve with a proximal section 334 having a first radius of curvature and a distal section 336 having a second radius of curvature that is larger than the first radius of curvature. In one embodiment, the first radius of curvature of the proximal section 334 of the curved member 322 is about 1.5 mm, and the second radius of curvature of the distal section 336 of the curved member 322 is about 2.5 mm. In one embodiment, the curved surgical fastener 320 has an outer diameter D3 of about 4.5 mm.

Referring to FIGS. 3C-3F, in one embodiment, the curved member 322 of the curved surgical fastener 320 lies in a single plane P3.

Referring to FIGS. 4A-4F, in one embodiment, a curved surgical fastener 420 preferably includes a curved member 422 having a proximal end 424 and a distal end 426. The curved surgical fastener 420 desirably includes a tissue penetrating end 428 located at the distal-most end of the curved member 422. The tissue penetrating end 428 is preferably tapered and/or curved. A distal end of the tissue penetrating end 428 preferably has an insertion tip 430 having a distal point 432 that facilitates insertion of the distal end 426 of the curved member 422 into tissue.

Figure 4A:
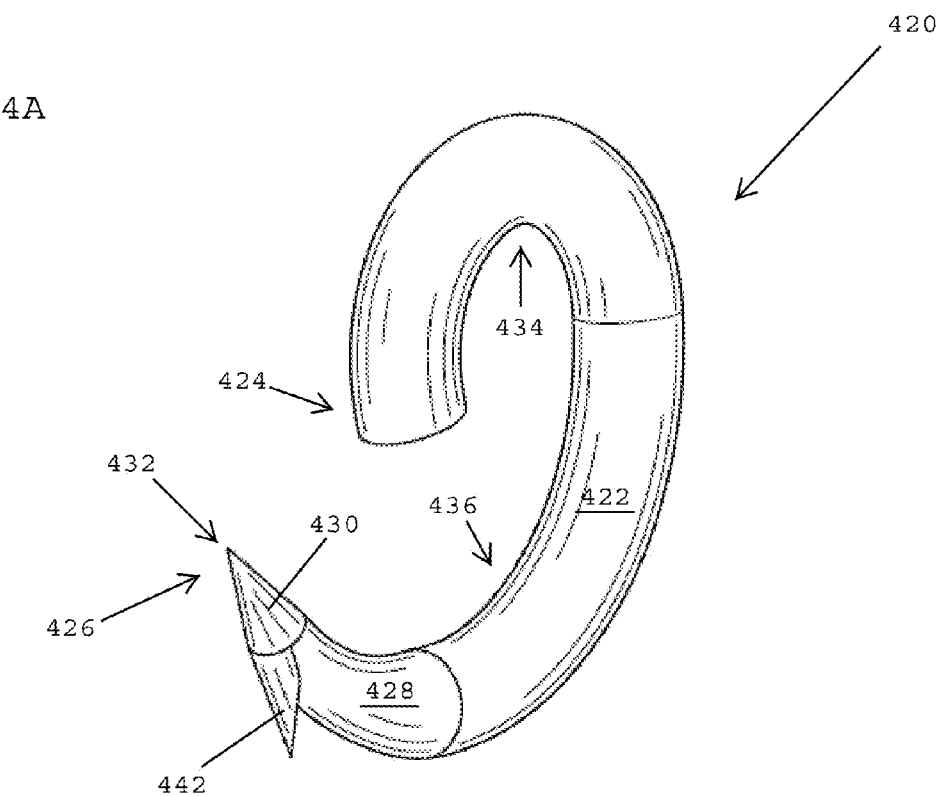
FIG. 4A is a perspective view of a curved surgical fastener, in accordance with a fourth embodiment of the present invention.
Figure 4B:
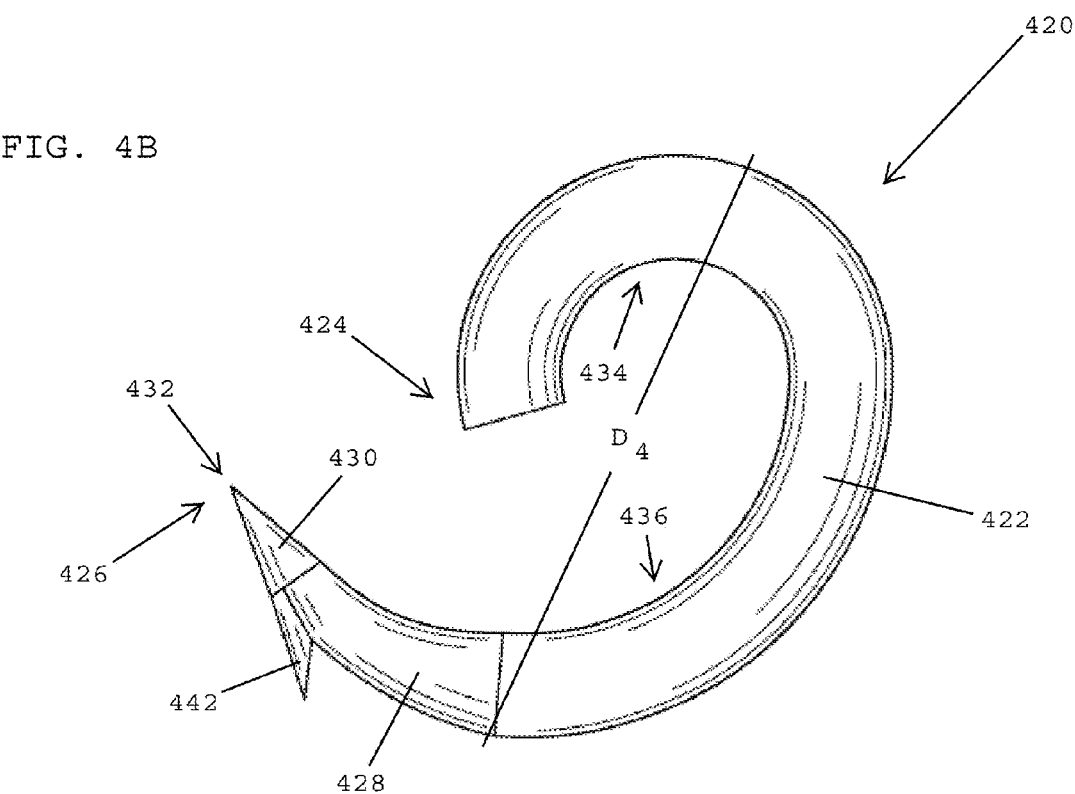
FIG. 4B is a front elevation view of the curved surgical fastener shown in FIG. 4A.

Referring to FIGS. 4A and 4B, in one embodiment, the curved surgical fastener 420 preferably includes a barb 442 projecting from the tissue penetrating end 428. The barb 442 desirably projects away from the distal end 426 of the curved member 422. After the insertion tip 430 is advanced into tissue, the barb 442 is adapted to hold the curved member 422 in place and prevent retraction and/or pullout of the curved member from the tissue.

In one embodiment, the curved member 422 has a total curvature between the proximal end 424 and the distal end 426 of less than 360 degrees. In one embodiment, the curved member defines a compound curve having a proximal section 434 with a first radius of curvature and a distal section 436 with a second radius of curvature that is different than the first radius of curvature. In one embodiment, the first radius of curvature is smaller than the second radius of curvature. In one embodiment, the first radius of curvature of the proximal section 434 of the curved member 422 is about 1.5 mm, and the second radius of curvature of the distal section 436 of the curved member 422 is about 2.5 mm. In one embodiment, the curved surgical fastener 420 has an outer diameter D4 of about 4.5 mm.

Referring to FIGS. 4C-4F, in one embodiment, the curved member 422 of the curved surgical fastener 420 lies in a single plane P4.

Referring to FIGS. 5A-5F, in one embodiment, a curved surgical fastener 520 has a curved member 522 having a larger radius of curvature than the curved surgical fastener shown in FIGS. 4A-4F. In one embodiment, the curved member 522 has a proximal end 524, a distal end 526, and a tissue penetrating end 528 located at the distal-most end of the curved member 522. The tissue penetrating end 528 is preferably curved and/or tapered. A distal end of the tissue penetrating end 528 desirably has an insertion tip 530 having a distal point 532 that facilitates insertion of the distal end 526 of the curved member 522 into tissue.

Figure 5A:
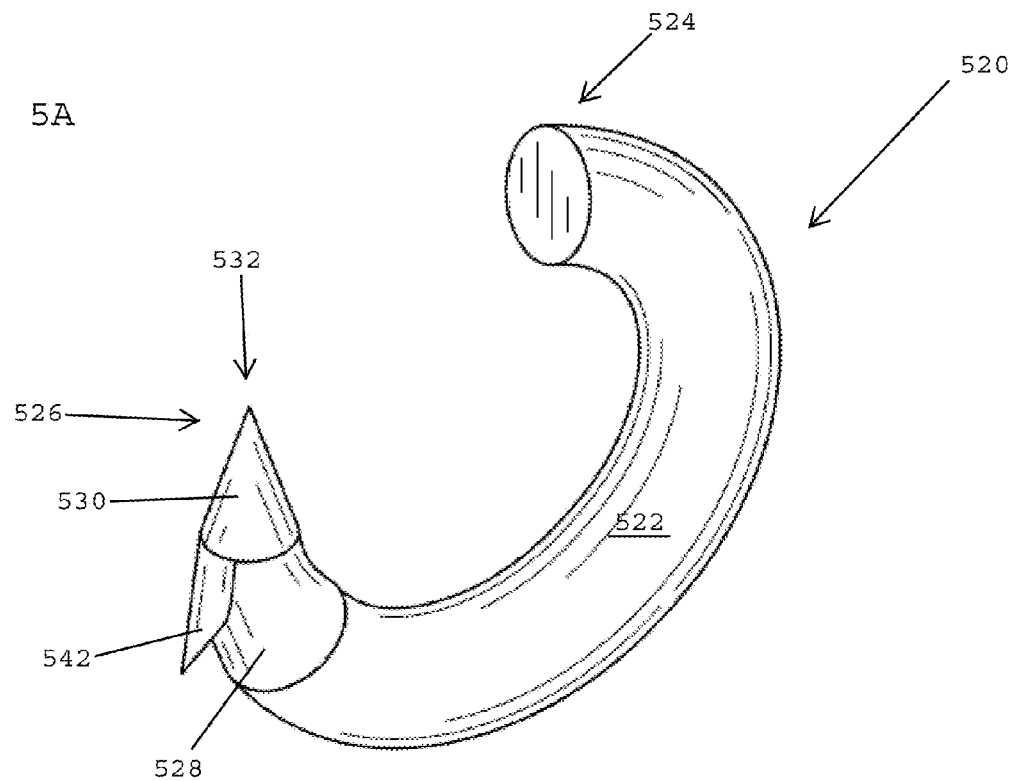
FIG. 5A is a perspective view of a curved surgical fastener, in accordance with a fifth embodiment of the present invention.
Figure 5B:
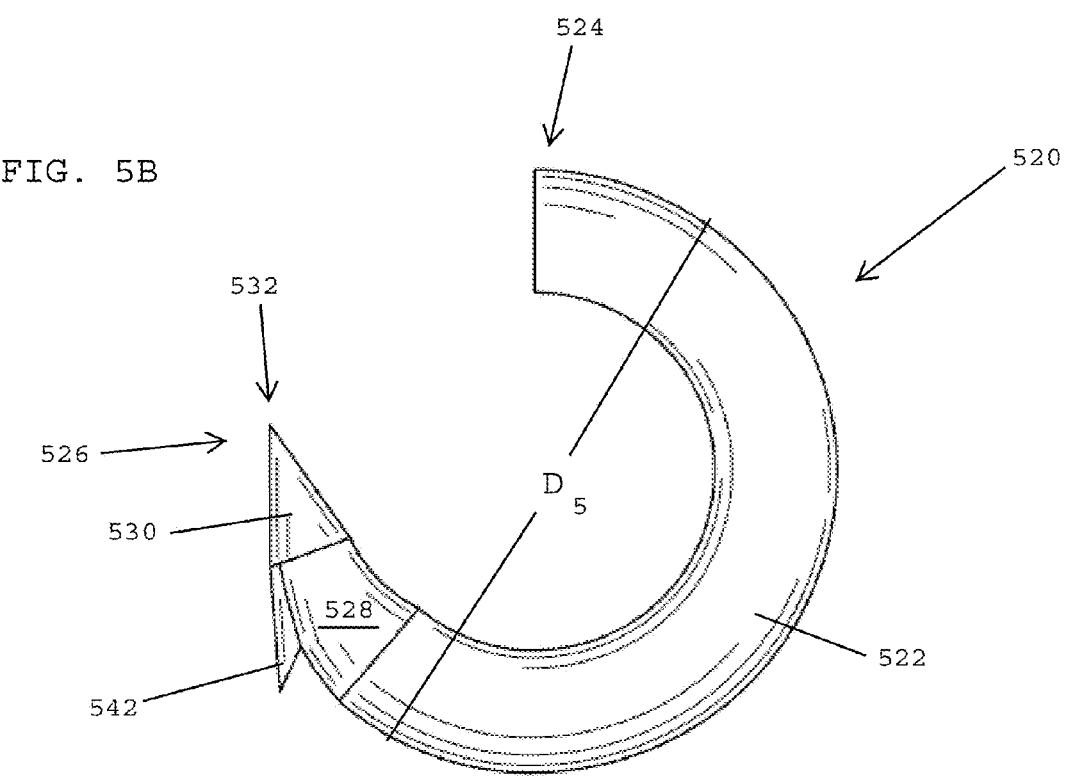
FIG. 5B is a front elevation view of the curved surgical fastener shown in FIG. 5A.
Figure 5C:
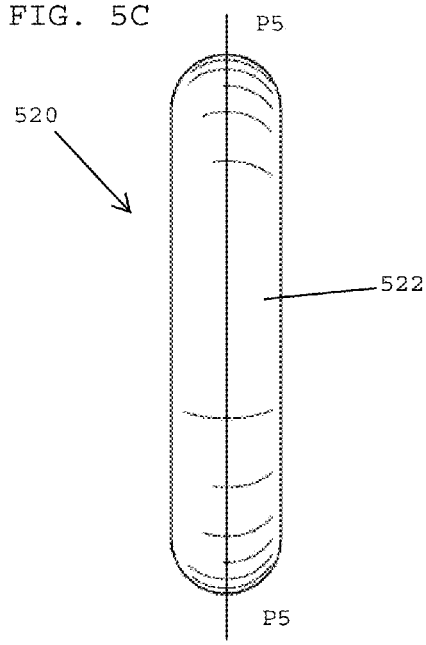
FIG. 5C is a right side view of the curved surgical fastener shown in FIG. 5A.
Figure 5D:
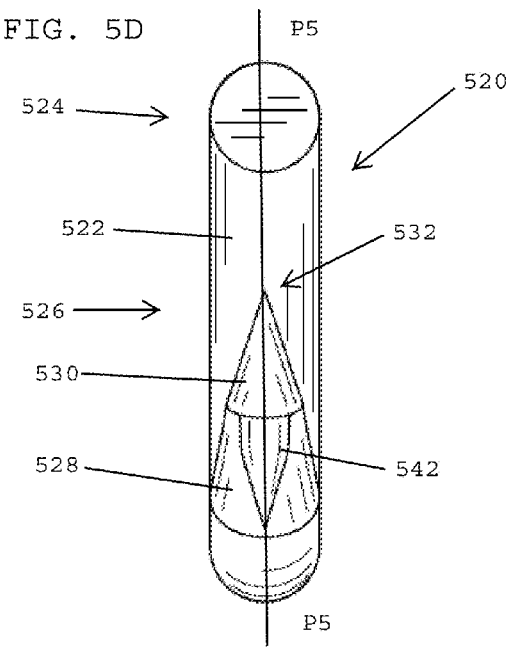
FIG. 5D is a left side view of the curved surgical fastener shown in FIG. 5A.
Figure 5E:
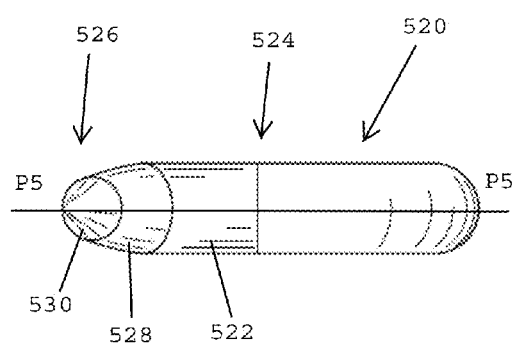
FIG. 5E is a top plan view of the curved surgical fastener shown in FIG. 5A.
Figure 5F:
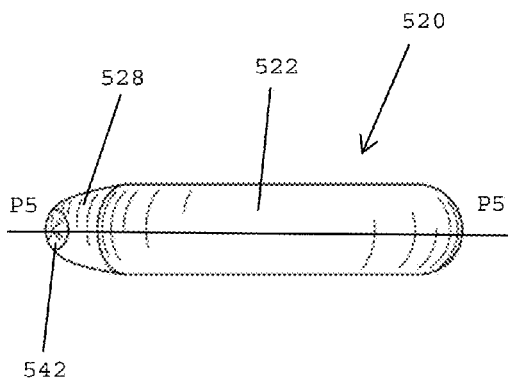
FIG. 5F is a bottom view of the curved surgical fastener shown in FIG. 5A.

Referring to FIGS. 5A and 5B, in one embodiment, the curved surgical fastener 520 preferably includes a barb 542 projecting from the tissue penetrating end 528. The barb 542 desirably projects away from the distal end 526 of the curved member 522. After the insertion tip 530 is advanced into tissue, the barb 542 is adapted to hold the curved member 522 in place and prevent retraction of the curved member from the tissue.

In one embodiment, the curved member 522 has a total curvature between the proximal end 524 and the distal end 526 of less than 360 degrees. In one embodiment, the curved member 522 has a constant radius of curvature between the proximal end 524 of the curved member and the tapered tissue penetrating end 528. Unlike the embodiments shown in FIGS. 1A-1F through 4A-4F above, the curved member 522 shown in FIGS. 5A-5F does not form a compound curve. In one embodiment, the radius of curvature of the curved member 522 is about 2.5 mm. In one embodiment, the curved surgical fastener 520 has an outer diameter D5 of about 5 mm.

Referring to FIGS. 5C-5F, in one embodiment, the curved member 522 of the curved surgical fastener 520 lies in a single plane P5.

Referring to FIGS. 6A-6F, in one embodiment, a curved surgical fastener 620 includes a curved member 622 having a proximal end 624, a distal end 626, and a tissue penetrating end 628 located at the distal-most end of the curved member 622. In one embodiment, the curved surgical fastener 620 has an insertion tip 630 located at the distal end of the tissue penetrating end 628. The distal-most end of the insertion tip 630 has a distal point 632 that facilitates insertion of the distal end 626 of the curved member 622 into tissue.

Figure 6A:
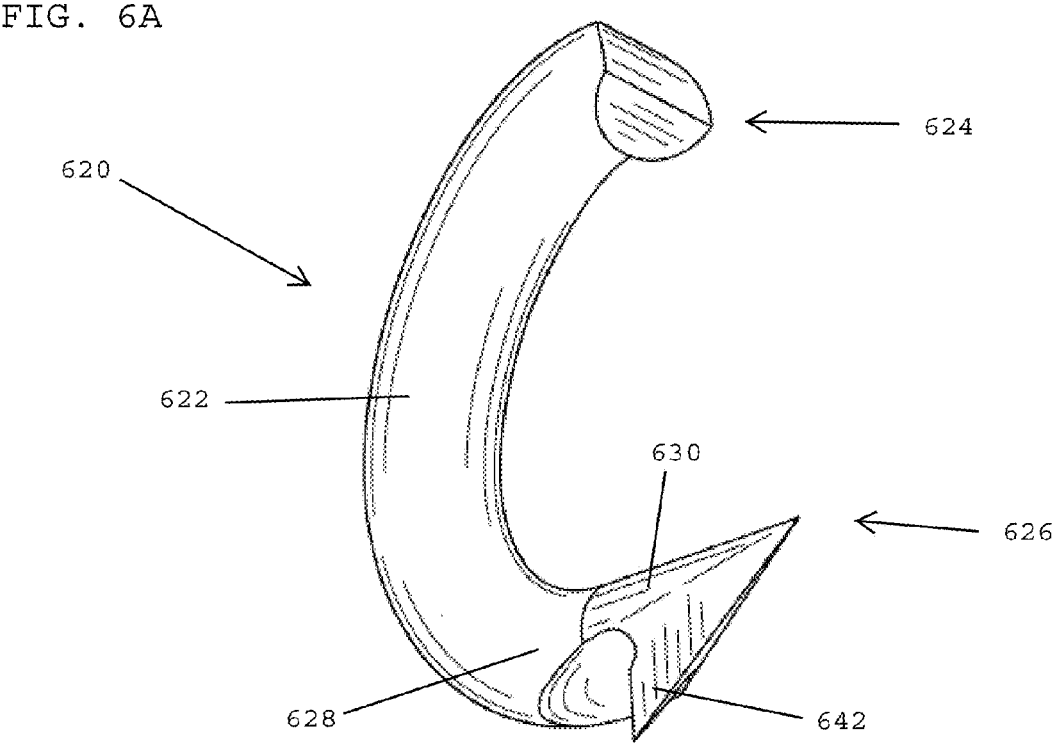
FIG. 6A is a perspective view of a curved surgical fastener, in accordance with a sixth embodiment of the present invention.
Figure 6B:
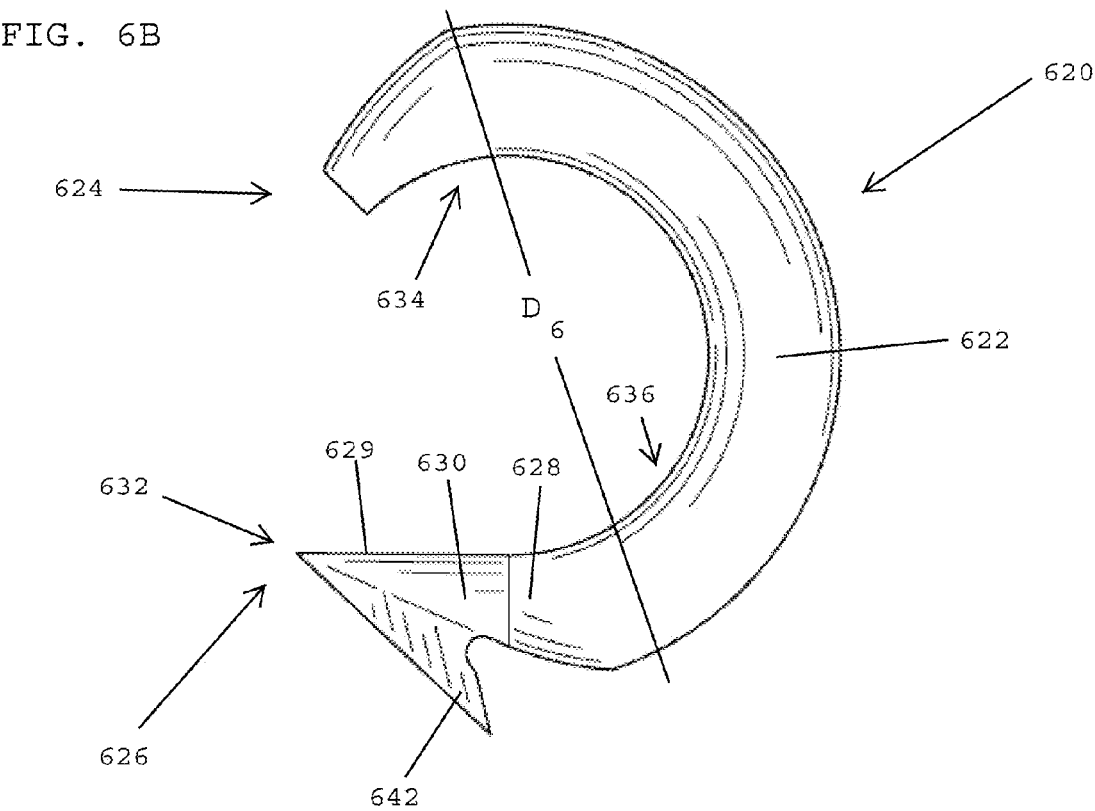
FIG. 6B is a front elevation view of the curved surgical fastener shown in FIG. 6A.

Referring to FIGS. 6A and 6B, in one embodiment, the curved surgical fastener 620 preferably includes a barb 642 projecting from the insertion tip 630. The barb 642 desirably projects away from the distal point 632 of the insertion tip 630. After the insertion tip 630 is advanced into tissue, the barb 642 is adapted to hold the curved member 622 in place and prevent retraction of the curved member from the tissue.

In one embodiment, the curved member 622 has a total curvature between the proximal end 624 and the distal end 626 of less than 360 degrees. In one embodiment, the curved member 622 forms a compound curve having a proximal section 634 with a first radius of curvature and a distal section 636 with a second radius of curvature that is different than the first radius of curvature. In one embodiment, the first radius of curvature is smaller than the second radius of curvature. In one embodiment, the first radius of curvature of the proximal section 634 of the curved member 622 is about 2.5 mm, and the second radius of curvature of the distal section 636 of the curved member 622 is about 2.5 mm. In one embodiment, the curved surgical fastener 620 has an outer diameter D6 of about 5 mm.

Referring to FIGS. 6C-6F, in one embodiment, the proximal end 624 of the curved member 622 lies in a first plane P6, and the distal end 626 of the curved member 622 lies in a second plane P6' that is offset from the first plane P6. The curved member 622 desirably has an intermediate section 625 that interconnects the respective proximal and distal ends 624, 626 of the curved member 622 as the curved member transitions from the first plane P6 to the second plane P6'. Although the present invention is not limited by any particular theory of operation, it is believed that providing a curved surgical fastener that extends into two different planes enhances the anchoring force of the fastener in tissue and makes it more difficult to extract the fastener from the tissue.

Referring to FIGS. 7A-7F, in one embodiment, a curved surgical fastener 720 includes a curved member 722 having a proximal end 724, a distal end 726, and a tissue penetrating end 728 located at the distal end of the curved member 722. The tissue penetrating end 728 is preferably tapered and/or curved. In one embodiment, the curved surgical fastener 720 has an insertion tip 730 located at the distal end of the tissue penetrating end 728. The distal-most end of the insertion tip 730 has a distal point 732 that facilitates insertion of the curved member 722 into tissue.

Figure 7A:
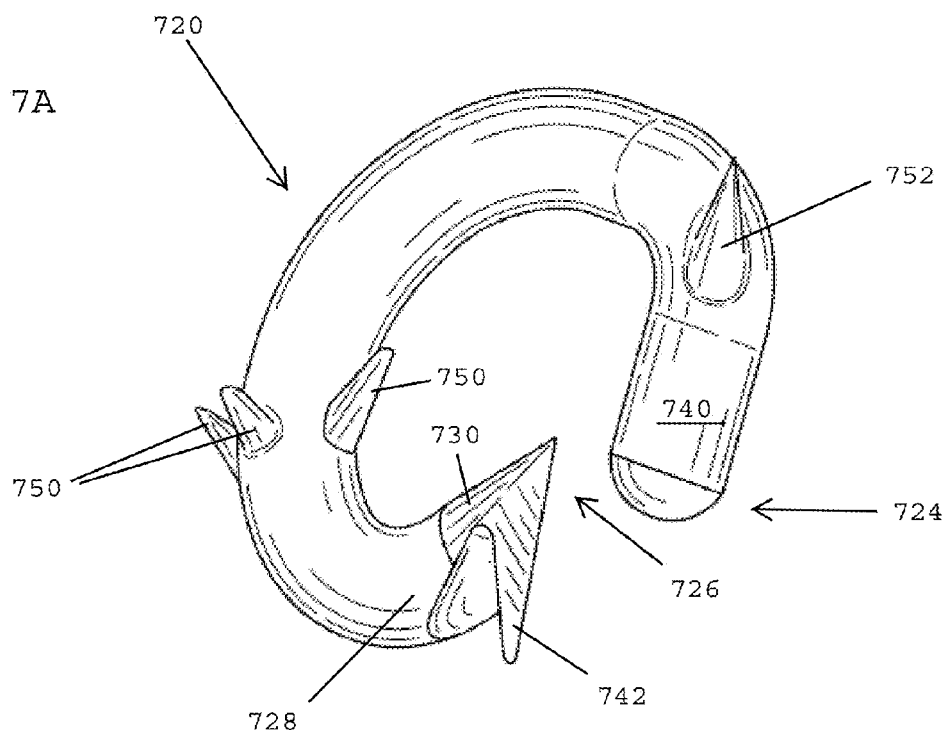
FIG. 7A is a perspective view of a curved surgical fastener, in accordance with a seventh embodiment of the present invention.
Figure 7B:
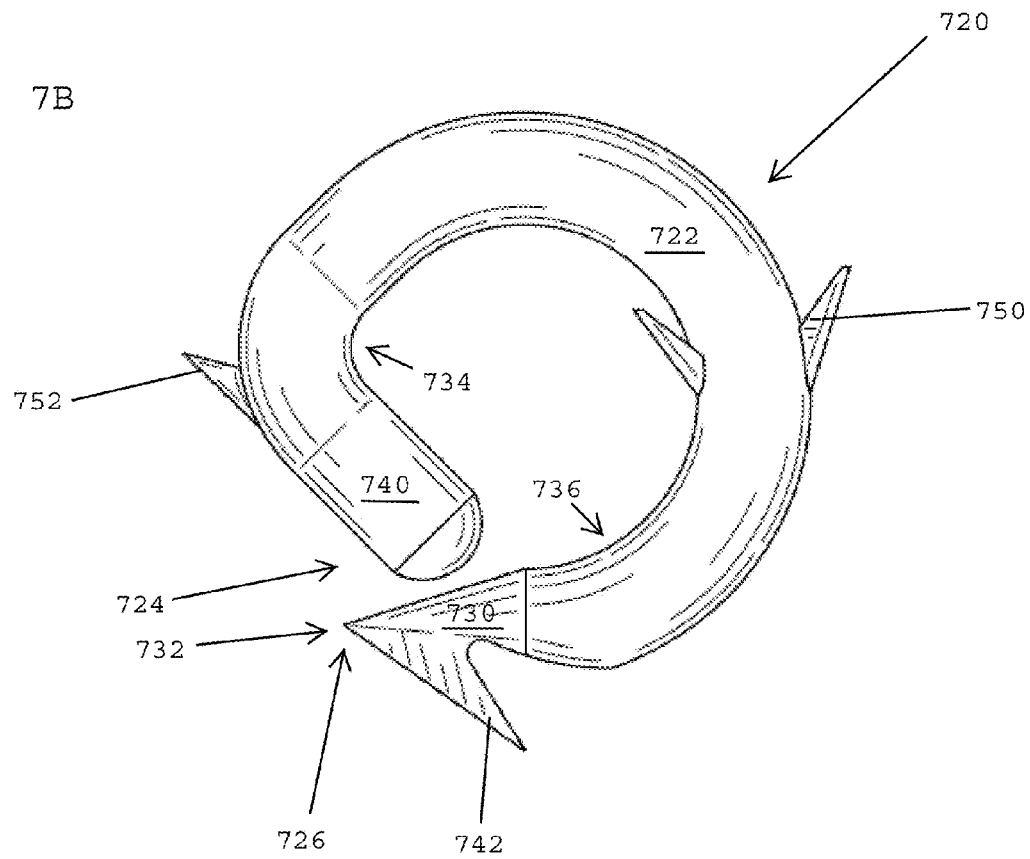
FIG. 7B is a front elevation view of the curved surgical fastener shown in FIG. 7A.

Referring to FIGS. 7A and 7B, in one embodiment, the curved surgical fastener 720 preferably includes a distal barb 742 projecting from the insertion tip 730. The distal barb 742 desirably projects away from the point 732 of the insertion tip 730. The curved surgical fastener 720 also desirably includes one or more intermediate barbs 750 projecting from an intermediate section 725 of the curved member 722, and a proximal barb 752 projecting from the proximal end 724 of the curved member 722. After the insertion tip 730 is advanced into tissue, the distal barb 742 and the one or more intermediate barbs 750 are adapted to hold the curved member 722 in place and prevent retraction of the curved member from the tissue. The proximal barb 752, which projects away from the proximal end of the curved member, is adapted to engage a surgical mesh for securing the surgical mesh to tissue.

In one embodiment, the proximal end 724 of the curved member 722 has a tang 740 projecting therefrom. The tang 740 may define a straight section of the device 720 and is adapted to engage a prosthetic device such as a surgical mesh for securing the surgical mesh to tissue.

In one embodiment, the curved member 722 has a total curvature between the proximal end 724 and the distal end 726 of less than 360 degrees. In one embodiment, the curved member 722 forms a compound curve having a proximal section 734 with a first radius of curvature and a distal section 736 with a second radius of curvature that is different than the first radius of curvature. In one embodiment, the first radius of curvature is smaller than the second radius of curvature. In one embodiment, the first radius of curvature of the proximal section 734 of the curved member 722 is smaller than the second radius of curvature of the distal section 736 of the curved member 722.

Referring to FIGS. 7C-7F, in one embodiment, the proximal end 724 of the curved member 722 lies in a first plane P7, and the distal end 726 of the curved member 722 lies in a second plane P7' that is offset from the first plane P7. The curved member 722 desirably has an intermediate section 725 that interconnects the respective proximal and distal sections 724, 726 of the curved member 722 as the curved member transitions from the first plane P7 to the second plane P7'.

In one embodiment, the curved surgical fastening devices are used for securing prosthetic devices such as surgical mesh to tissue. In one embodiment, after a surgical mesh is placed over tissue, the insertion tip at the distal end of a curved member is advanced through the mesh and into the tissue. When properly inserted into tissue, the distal end of the curved member is disposed within the tissue and the proximal end of the curved member is in contact with the surgical mesh for securing the surgical mesh to tissue.

Figure 8A:
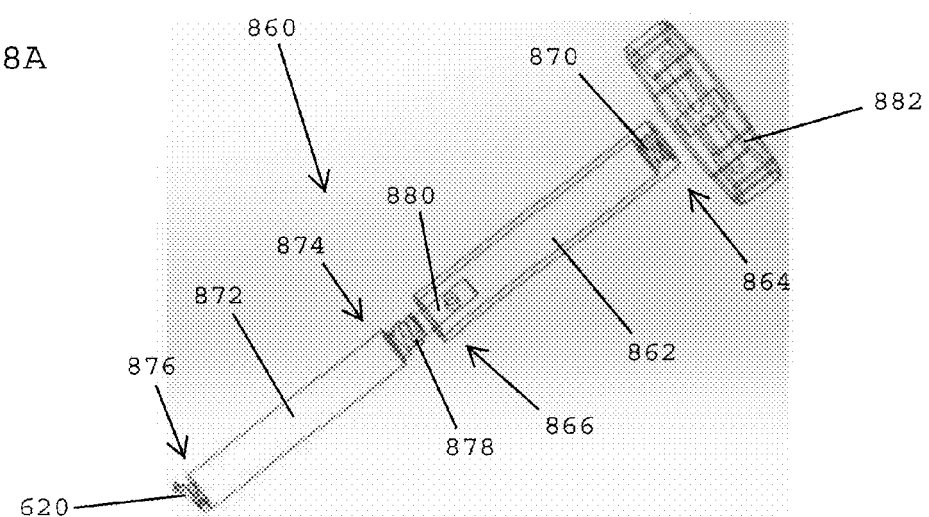
FIG. 8A shows an exploded view of an applicator instrument for dispensing curved surgical fasteners, in accordance with one embodiment of the present invention.

In one embodiment, an applicator instrument may be used for inserting the curved surgical fastening devices into tissue. Referring to FIG. 8A, in one embodiment, an applicator instrument 860 preferably has an outer shaft 862 having a proximal end 864, a distal end 866 and a central conduit 868 extending from the proximal end to the distal end of the outer shaft. The outer shaft 862 has internal threads 870 located at the proximal end of the outer shaft 862. The applicator instrument 860 preferably has an inner shaft 872 having a proximal end 874 and a distal end 876. The proximal end 874 of the inner shaft 872 has external threads 878 that are adapted to mesh with the internal threads 870 of the outer shaft 862 for connecting the outer and inner shafts together.

In one embodiment, an actuating rod 880 desirably extends from the proximal end 874 of the inner shaft 872. The applicator instrument 860 includes a handle 882 that is securable to the proximal end of the actuating shaft 880. A pin may be used for connecting the handle and the actuating rod together. In one embodiment, rotating the handle 882 simultaneously rotates the actuating rod 880 and the inner shaft 872. As the inner shaft 872 rotates relative to the outer shaft 862, the external threads 878 on the inner shaft 872 engage the internal threads 870 on the outer shaft 862 for moving the inner shaft toward the distal end of the outer shaft.

Figure 8B:
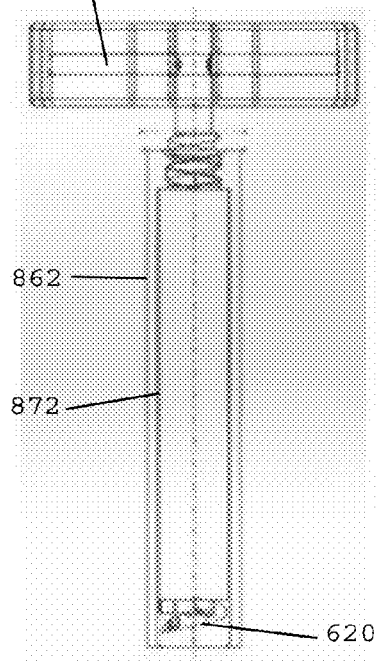
FIGS. 8B-8C show a method of using the applicator instrument of FIG. 8A for dispensing curved surgical fasteners, in accordance with one embodiment of the present invention.

FIG. 8B shows the applicator instrument 860 of FIG. 8A with the inner shaft 872 in a retracted position relative to the outer shaft 862. When the inner shaft 872 is retracted, the underside of the handle 882 is spaced from the proximal end 864 of the outer shaft 862. A curved surgical fastening device, such as the curved surgical fastening device 620 shown FIGS. 6A-6F of the present patent application, is loaded onto the distal end of the inner shaft 872.

Figure 8C:
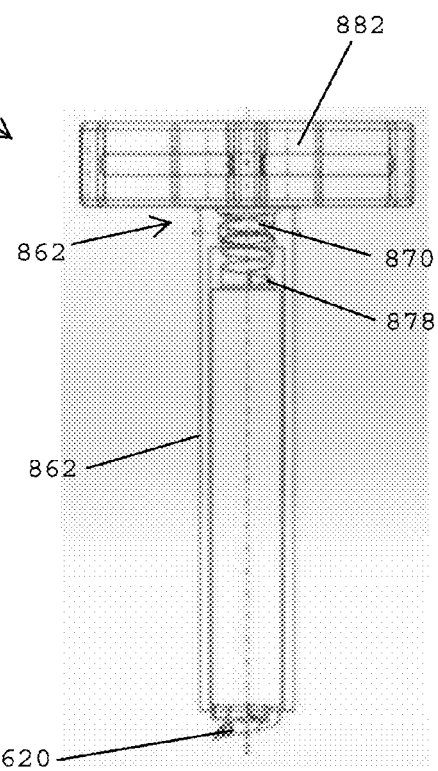

Referring to FIG. 8C, in one embodiment, when the handle 882 is rotated in a clockwise or corkscrew-like manner, the actuating rod 880 is rotated about its longitudinal axis, which is turn rotates the inner shaft 872 about its longitudinal axis relative to the outer shaft 862. The engagement of the inner threads 870 of the outer shaft 862 with the outer threads 878 of the inner shaft 872 moves the inner shaft toward the distal end 866 of the outer shaft 862 until the curved surgical fastening device 620 is advanced through a surgical mesh and into tissue. In one embodiment, the curved surgical fastener is advanced into the tissue via a corkscrew-like motion. Distal advancement of the inner shaft 872 relative to the outer shaft 862 is halted when the underside of the handle 882 engages the proximal end 864 of the outer shaft 862.

Figure 9:
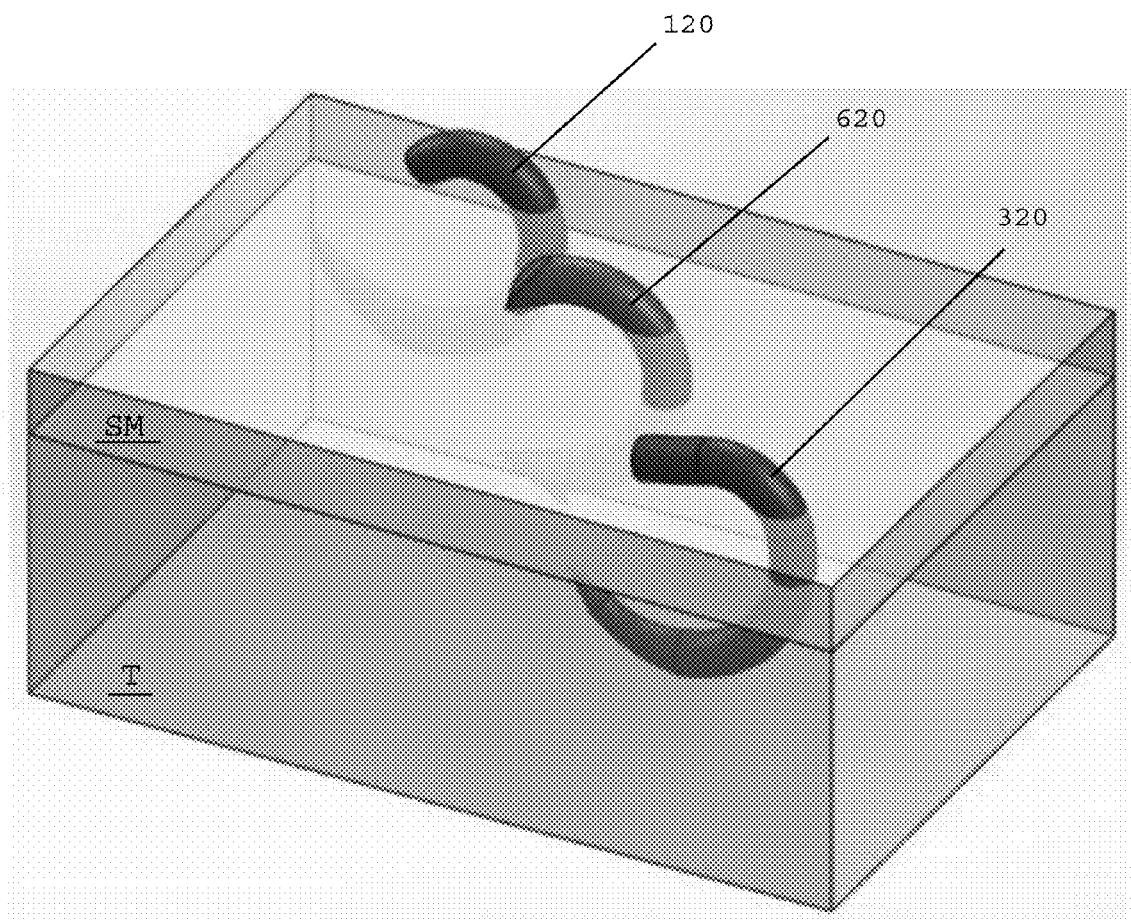
FIG. 9 shows a perspective view of curved surgical fasteners securing a surgical mesh to tissue, in accordance with one embodiment of the present invention.
Figure 10:
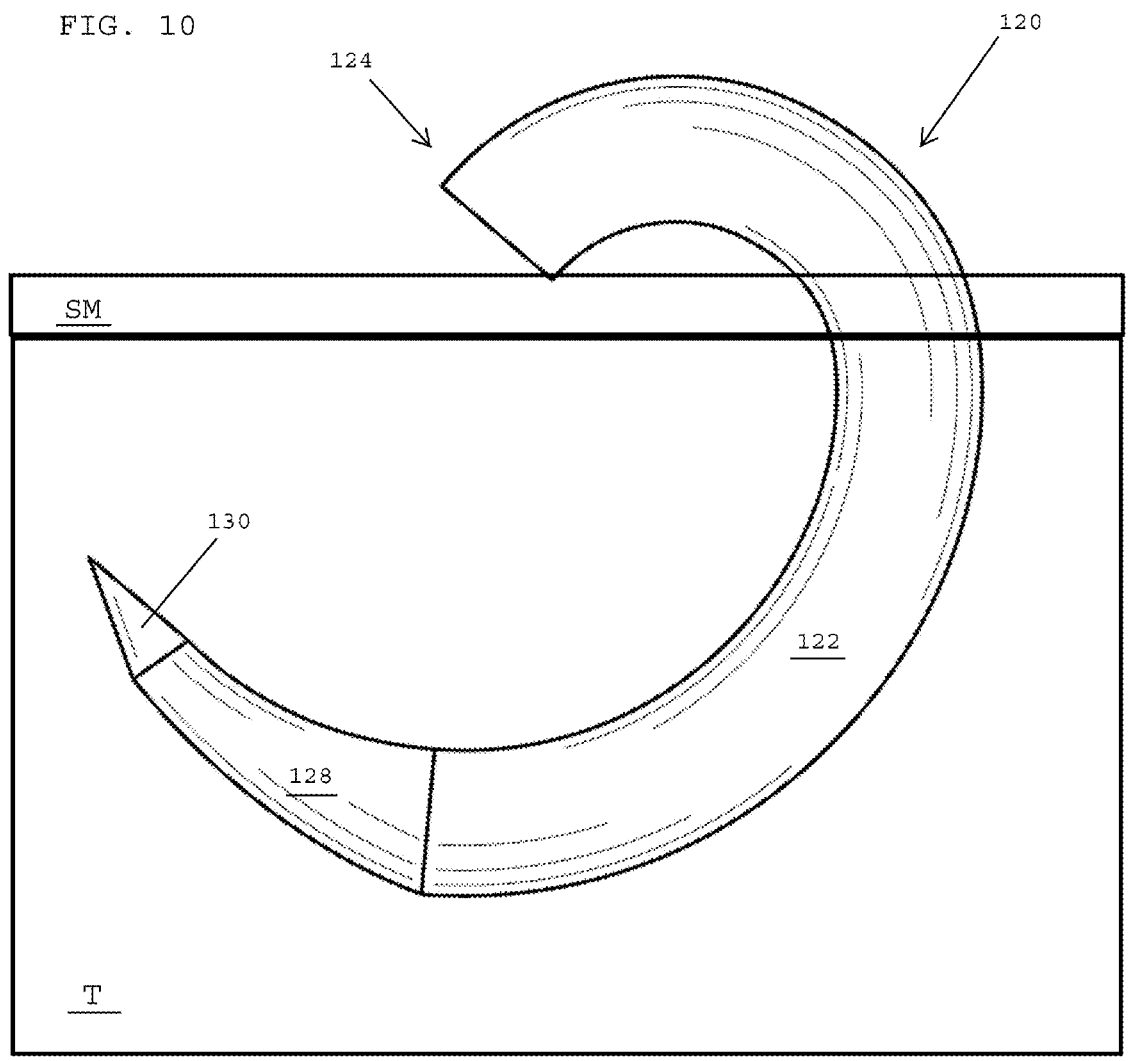
FIG. 10 shows a curved surgical fastener having a pointed distal end securing a surgical mesh to tissue, in accordance with one embodiment of the present invention.

Referring to FIGS. 9 and 10, in one embodiment, a prosthetic device such as surgical mesh SM is positioned over tissue T. A first curved surgical fastening device 120 similar to that shown and described above in FIGS. 1A-1F is inserted through the surgical mesh SM and into tissue T so that the insertion tip 130, the tissue penetrating end 128, and the distal end of the curved member are disposed within the tissue T and the proximal end 124 of the curved member 122 overlies the top surface of the surgical mesh SM. The proximal end 124 of the curved member 22 preferably engages the surgical mesh SM for securing the surgical mesh to the tissue T.

Figure 11:
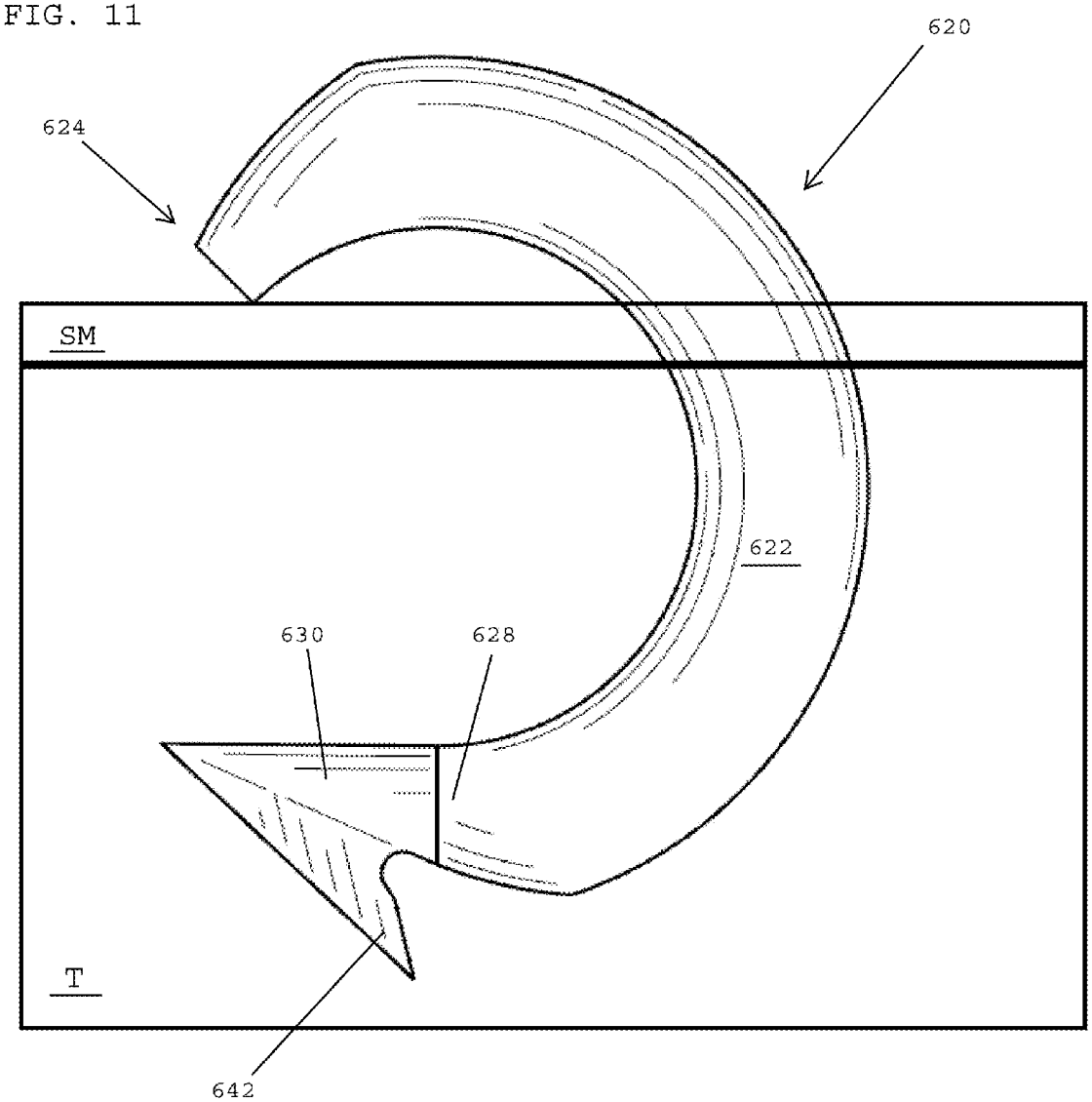
FIG. 11 shows a curved surgical fastener having a barb at a distal end thereof securing a surgical mesh to tissue, in accordance with one embodiment of the present invention.

Referring to FIGS. 9 and 11, in one embodiment, a second curved surgical fastening device 620 similar to that shown and described above in FIGS. 6A-6F is inserted through the surgical mesh SM and into tissue T so that the insertion tip 630, the tissue penetrating end 628, and the distal end of the curved member 622 are disposed within the tissue and the proximal end 624 of the curved member 622 overlies the top surface of the surgical mesh SM. The curved surgical fastening device 620 has a barb 642 that projects from the insertion tip 630. After the curved surgical fastening device 620 has been inserted into the tissue T, the barb 642 preferably prevents the curved member 622 from being retracted from the tissue T. The proximal end 624 of the curved member 622 preferably engages the surgical mesh SM for securing the surgical mesh to the tissue T.

Figure 12:
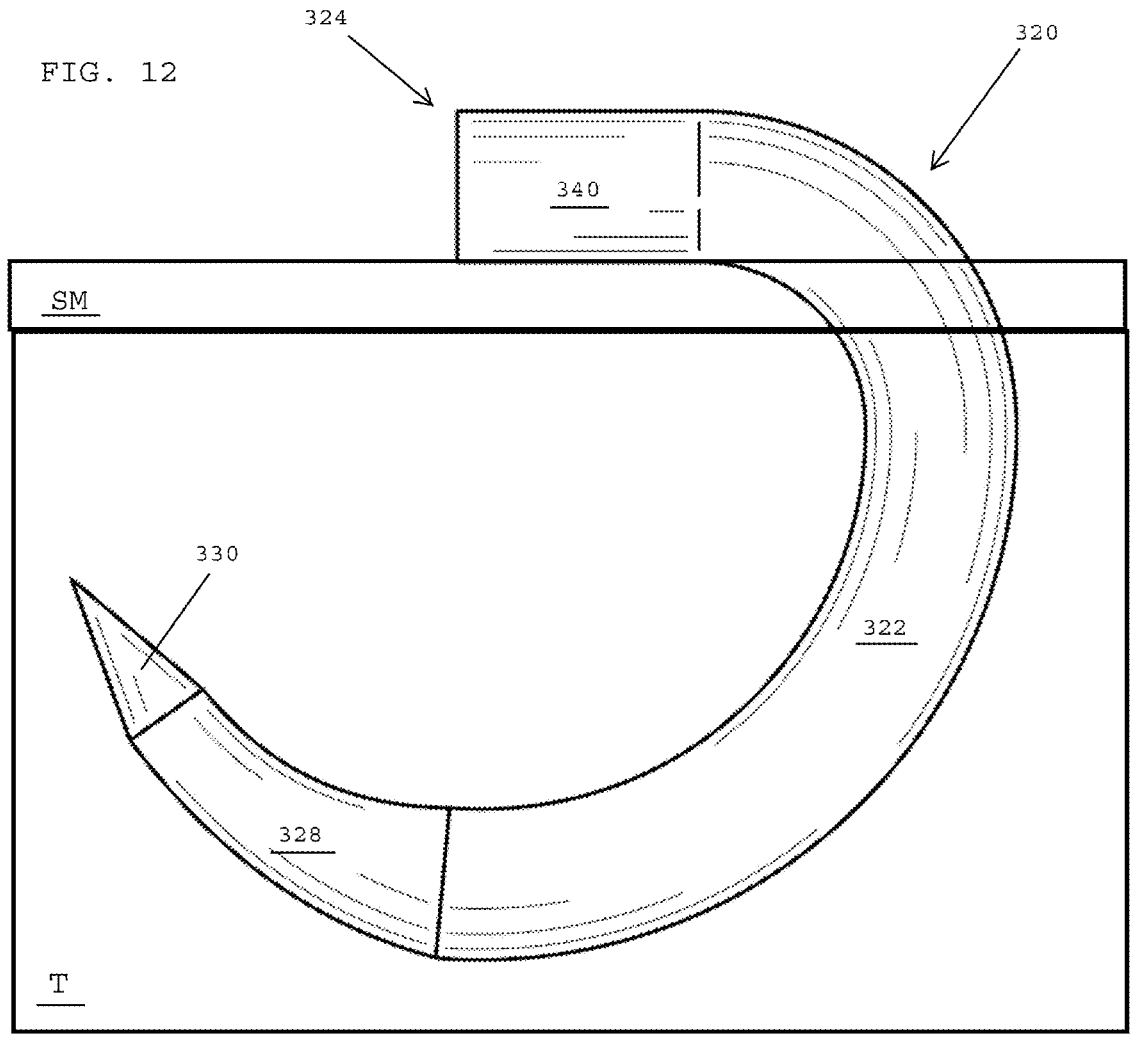
FIG. 12 shows a curved surgical fastener having a pointed distal end and a tang at a proximal end securing a surgical mesh to tissue, in accordance with one embodiment of the present invention.

Referring to FIGS. 9 and 12, in one embodiment, a third curved surgical fastening device 320 similar to that shown and described above in FIGS. 3A-3F is inserted through the surgical mash SM and into tissue T so that the insertion tip 330, the tissue penetrating end 328, and the distal end of the curved member 322 are disposed within the tissue T and the tang 340 at the proximal end 324 of the curved member 322 overlies the top surface of the surgical mesh SM. After the curved surgical fastening device 320 has been inserted into the tissue T, the tang 340 at the proximal end 324 of the curved member 322 preferably engages the surgical mesh SM for securing the surgical mesh to the tissue T.

The dimensions of the curved members disclosed herein (e.g., radius of curvature and diameter) may change depending upon the materials used to make the surgical fasteners, such as a polymer material versus a metal. The dimensions of the curved members may also change depending upon where in the body the surgical fasteners are intended to be used. In one embodiment, the pitch of the helix may be less in instances where a shallow tissue penetration is required.

In one embodiment, the radii of curvature of the curved members may be smaller and the material diameters may be less if the material used is a metal.

Although the present invention is not limited by any particular theory of operation, it is believed that providing curved surgical fasteners will provide enhanced control over the penetration depth and pull force. The curved design provides a low profile shallow depth anchor useful for securing surgical mesh to tissue in areas where the tissue is relatively thin while still attaining sufficient anchoring strength for insuring that the fastening devices may not be easily extracted from tissue. The curved surgical fastening devices may be used to penetrate surgical mesh and affix to soft tissue anatomical structures, such as a Cooper's ligament or fascia that cover bone. The barbs projecting from the curved members provide additional anchoring force.

In one embodiment, the applicator instrument of the present invention may be used to repair of a defect, such as an inguinal hernia, located in inguinal tissue such as the inguinal floor. Generally, an inguinal hernia may be accessed through the iliacus muscle. As can be well appreciated, a network of vessels and nerves exist in the area of a typical inguinal hernia, which requires a surgeon to conduct a hernia repair with great skill and caution. For instance, in the transverse abdominis aponeurosis, an internal ring permits gastric vessels and Vas deferens to extend therethrough over an edge of inguinal ligament. A femoral canal is located near the Cooper's ligament and contains external iliac vessels and inferior epigastric vessels.

In many cases, the edge of the inguinal ligament and the Cooper's ligament serve as anatomical landmarks and support structures for supporting surgical fasteners such as those mentioned previously. The area containing the external iliac vessels and the Vas deferens may be commonly known as "the Triangle of Doom" to surgeons. Accordingly, care must be taken when performing dissection, suturing or fastening within this area.

A prosthetic or a surgical mesh patch may be placed over the inguinal hernia. The mesh patch may have any desired configuration, structure or material. In one embodiment, the mesh patch may be made of PROLENE™ (a well-known polymer made of fibers) and preferably configured as mesh.

The mesh patch may be placed over the inguinal hernia for providing a sufficient barrier to internal viscera (not shown) of the abdomen which would otherwise have a tendency to protrude through the inguinal hernia and cause the patient a great deal of pain and discomfort. After the mesh patch has been placed onto the inguinal floor, the mesh patch is ready for attachment to the inguinal floor. The curved surgical fastening devices disclosed herein are desirably utilized for attaching the mesh to the inguinal floor.

The headings used herein are for organizational purposes only and are not meant to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

While the foregoing is directed to embodiments of the present invention, other and further embodiments of the invention may be devised without departing from the basic scope thereof. As such, the scope of the present invention is to be limited only as set forth in the appended claims.

What is claimed is:

1. A curved surgical fastener for anchoring medical devices to tissue comprising:
    a curved member having a proximal end and a distal end; and
    a tissue penetrating end at said distal end of said curved member, wherein said curved member has a total curvature of less than 360 degrees between said proximal and distal ends, and wherein said proximal end, said distal end, and said tissue penetrating end at said distal end of said curved member lie in a single plane; wherein said curved member comprises a compound curve; and wherein a proximal section of said curved member has a first radius of curvature and a distal section of said curved member has a second radius of curvature that is different than said first radius of curvature.

2. The curved surgical fastener as claimed in claim 1, wherein said proximal end of said curved member defines a proximal end of said curved surgical fastener and said tissue penetrating end at said distal end of said curved member defines a distal end of said curved surgical fastener.

3. The curved surgical fastener as claimed in claim 1, wherein said tissue penetrating end is curved.

4. The curved surgical fastener as claimed in claim 1, wherein said proximal end of said curved member comprises a tang.

5. The curved surgical fastener as claimed in claim 4, wherein said tang is straight.

6. The curved surgical fastener as claimed in claim 1, wherein said curved member comprises an absorbable material.

7. A curved surgical fastener for anchoring medical devices to tissue comprising:
    a curved member having a proximal end and a distal end; said curved member defining a compound curve and having a total curvature of less than 360 degrees between said proximal and distal ends of said curved member; and
    said distal end of said curved member including a tissue penetrating end having an insertion tip with a distal point, wherein said proximal end, said distal end, and said tissue penetrating end of said curved member lie in a single plane; wherein said curved member comprises a compound curve; and wherein a proximal section of said curved member has a first radius of curvature and a distal section of said curved member has a second radius of curvature that is different than said first radius of curvature.

8. The curved surgical fastener as claimed in claim 7, wherein said proximal end of said curved member defines a proximal-most end of said curved surgical fastener and said tissue penetrating end at said distal end of said curved member defines a distal-most end of said curved surgical fastener.

9. The curved surgical fastener as claimed in claim 7, wherein said tissue penetrating end is curved.

10. The curved surgical fastener as claimed in claim 7, wherein said proximal end of said curved member comprises a tang.

11. The curved surgical fastener as claimed in claim 10, wherein said tang is straight.

12. The curved surgical fastener as claimed in claim 7, wherein said curved member comprises an absorbable material.

* * * * *